United States Patent
Imai et al.

(10) Patent No.: US 11,592,385 B2
(45) Date of Patent: Feb. 28, 2023

(54) MONITORING DEVICE AND MONITORING SYSTEM

(71) Applicant: CYTORONIX INC., Kawasaki (JP)

(72) Inventors: Kaita Imai, Edogawa (JP); Shouhei Kousai, Yokohama (JP); Michihiko Nishigaki, Kawasaki (JP)

(73) Assignee: CYTORONIX INC., Kawasaki (JP)

( * ) Notice: Subject to any disclaimer, the term of this patent is extended or adjusted under 35 U.S.C. 154(b) by 55 days.

(21) Appl. No.: 17/019,789

(22) Filed: Sep. 14, 2020

(65) Prior Publication Data

US 2020/0408663 A1 Dec. 31, 2020

Related U.S. Application Data

(63) Continuation of application No. PCT/JP2020/009864, filed on Mar. 6, 2020, which is
(Continued)

(30) Foreign Application Priority Data

Mar. 14, 2019 (JP) ............................. JP2019-047258

(51) Int. Cl.
*G01N 15/14* (2006.01)
*G01N 15/00* (2006.01)

(52) U.S. Cl.
CPC . *G01N 15/1434* (2013.01); *G01N 2015/0065* (2013.01); *G01N 2015/144* (2013.01)

(58) Field of Classification Search
CPC ....... G01N 15/1434; G01N 2015/0065; G01N 2015/144
(Continued)

(56) References Cited

U.S. PATENT DOCUMENTS 5,307,161 A 4/1994 Miyamoto
5,347,122 A 9/1994 Ansorge et al.
(Continued)

FOREIGN PATENT DOCUMENTS

EP 3 521 893 A1 8/2019
JP 4-316478 A 11/1992
(Continued)

OTHER PUBLICATIONS

Jang, B. et al., "A CMOS Fluorescent-Based Biosensor Microarray," 2009 IEEE International Solid-State Circuits Conference (ISSCC 2009), Session 25 / Medical / 25.5, 2009, 3 pages.
(Continued)

*Primary Examiner* — Tarifur R Chowdhury
*Assistant Examiner* — Omar H Nixon
(74) *Attorney, Agent, or Firm* — Oblon, McClelland, Maier & Neustadt, L.L.P.

(57) ABSTRACT

According to one embodiment, a monitoring device includes a detector unit including an image transfer element comprising an incident surface which allows light to enter from a light-transmissive base material on which a microbody is placed and an emission surface which emits the light entering from the incident surface, which transfers two-dimensional image data of the microbody to a semiconductor optical sensor, and the semiconductor optical sensor which receives light from the emission surface.

36 Claims, 25 Drawing Sheets

Related U.S. Application Data a continuation of application No. 16/562,798, filed on Sep. 6, 2019, now abandoned.

(58) Field of Classification Search
USPC ............................................. 365/343
See application file for complete search history.

(56) References Cited

U.S. PATENT DOCUMENTS

| | | | |
|---|---|---|---|
| 2008/0297774 A1* | 12/2008 | Jiang | G01B 11/06 356/123 |
| 2009/0161100 A1 | 6/2009 | Minot et al. | |
| 2012/0223214 A1 | 9/2012 | Lee et al. | |
| 2012/0223217 A1 | 9/2012 | Zheng et al. | |
| 2014/0133702 A1 | 5/2014 | Zheng et al. | |
| 2014/0193892 A1* | 7/2014 | Mohan | G01N 15/1434 435/287.2 |
| 2014/0273188 A1* | 9/2014 | Mohan | G02B 21/125 422/82.05 |
| 2017/0268982 A1* | 9/2017 | Kousai | G01N 33/4833 |
| 2019/0062689 A1* | 2/2019 | Ariga | H04N 5/30 |
| 2019/0219809 A1 | 7/2019 | Mochizuki et al. | |
| 2020/0124626 A1* | 4/2020 | Bittner | C12M 41/48 |

FOREIGN PATENT DOCUMENTS

| | | | |
|---|---|---|---|
| JP | 2002-286643 A | | 10/2002 |
| JP | 2004045668 A | * 2/2004 | ........... G03G 9/0827 |
| JP | 2011-188180 A | | 9/2011 |
| JP | 2014-515179 A | | 6/2014 |
| JP | 2018134035 A | * 8/2018 | |
| WO | WO 2014/040730 A1 | | 3/2014 |
| WO | WO 2018/062215 A1 | | 4/2018 |

OTHER PUBLICATIONS

Sasagawa, K. et al., "Wide field-of-view lensless fluorescence imaging device with hybrid bandpass emission filter," AIP Advances, vol. 9, No. 3 Mar. 8, 2019, 9 pages.

Sasagawa, K. et al., "Lensless CMOS Imaging Device for Fluorescent and Non-Fluorescent Measurements for Digital ELISA," (with English translation), IEEJ Transactions on Sensors and Micromachines, vol. 136, No. 1, 2016, 13 pages.

Notice of Reasons for Refusal dated Dec. 6, 2022 in corresponding Japanese Patent Application No. 2021-173152 (with English translation)(8 pages).

Partial Supplementary European Search Report dated Dec. 2, 2022, in Application No. EP 20 77 0808, 22 pages.

P. Kozma, et al., "A Novel Fluorescent Microarray Reader for Point-of-Care Diagnostic", Biosensors and Bioelectronics, vol. 47, 2013, pp. 415-420.

A. Ozcan, "Lensless Imaging and Sensing", Annual Review of Biomedical Enginerring, vol. 18, No. 1, 2016, pp. 77-102.

* cited by examiner

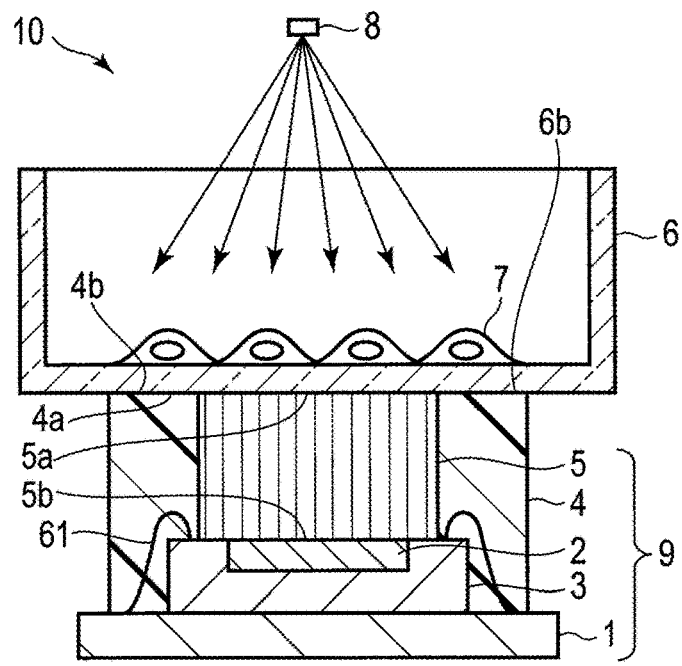
F I G. 1
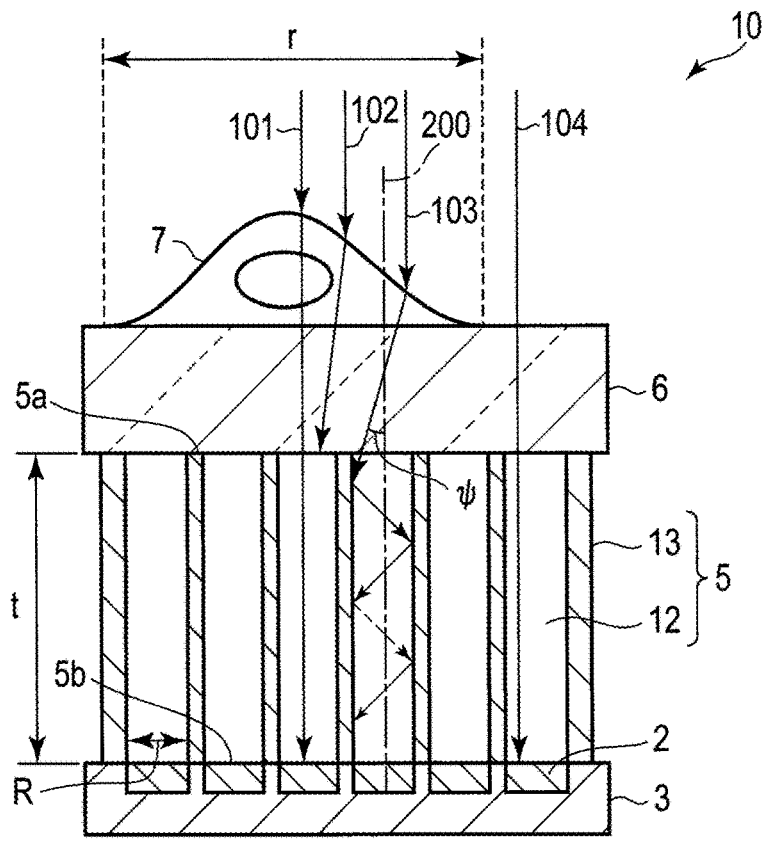
F I G. 2

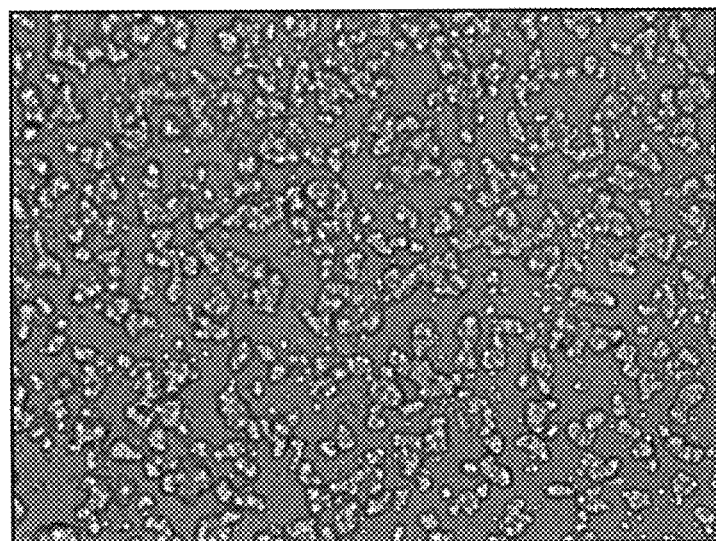
100μm
F I G. 5
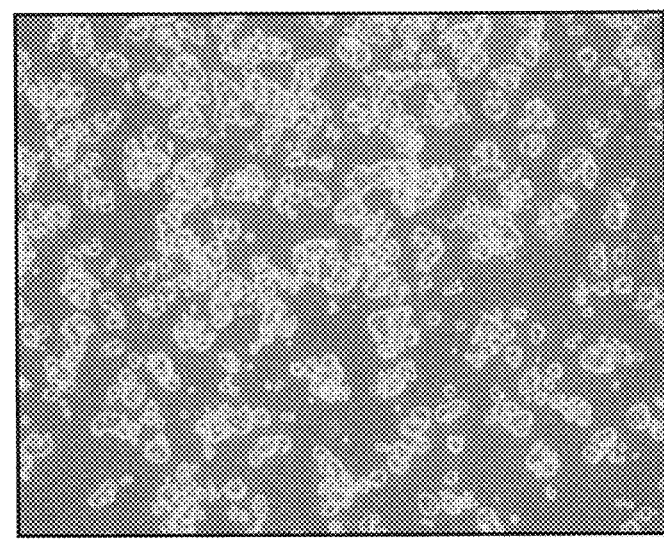
100μm
F I G. 6

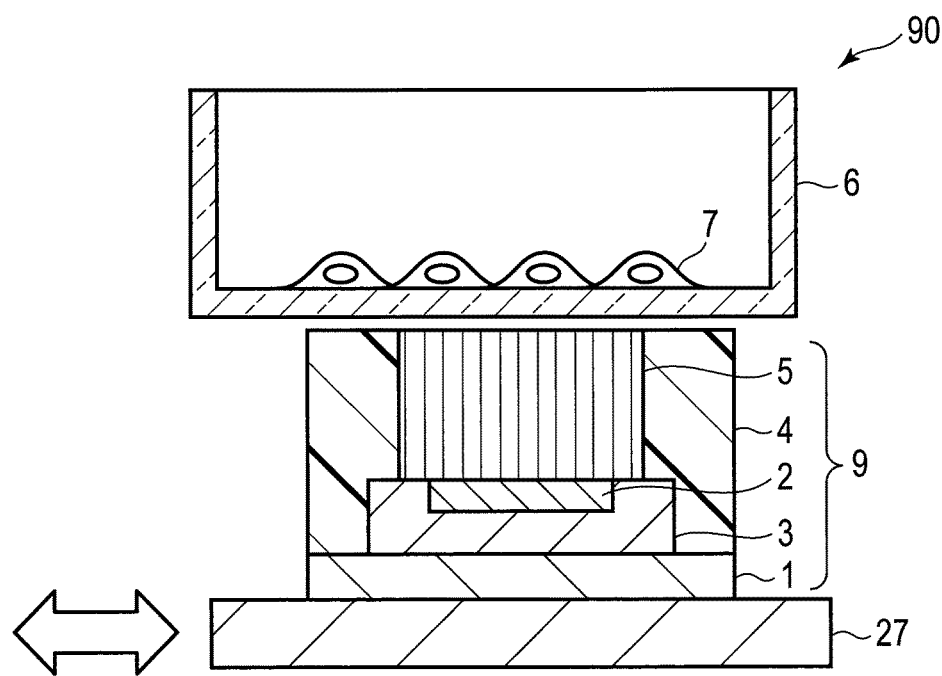
F I G. 16
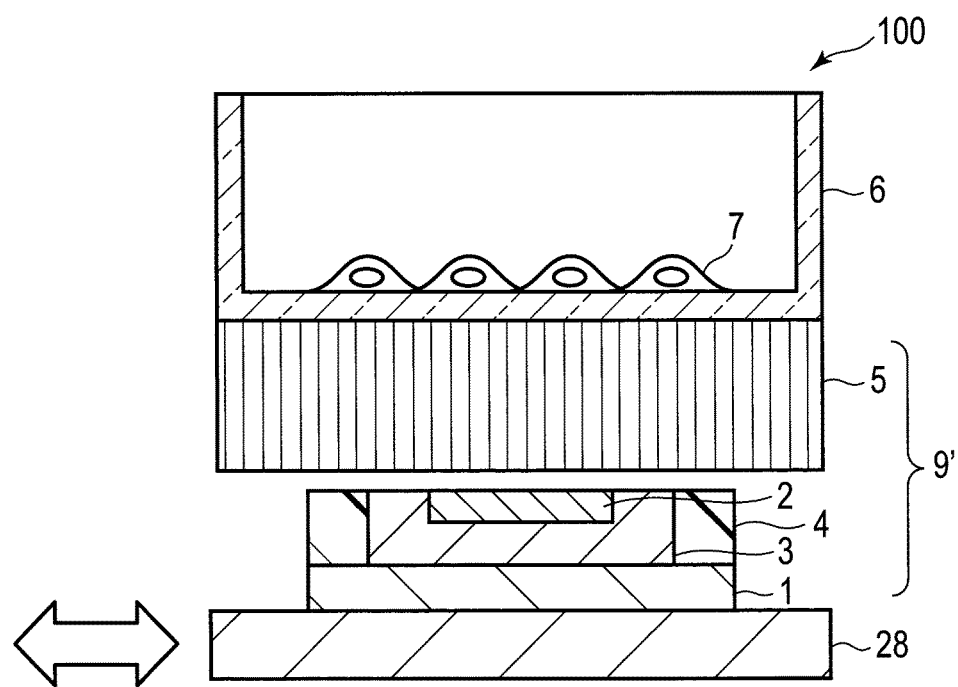
F I G. 17

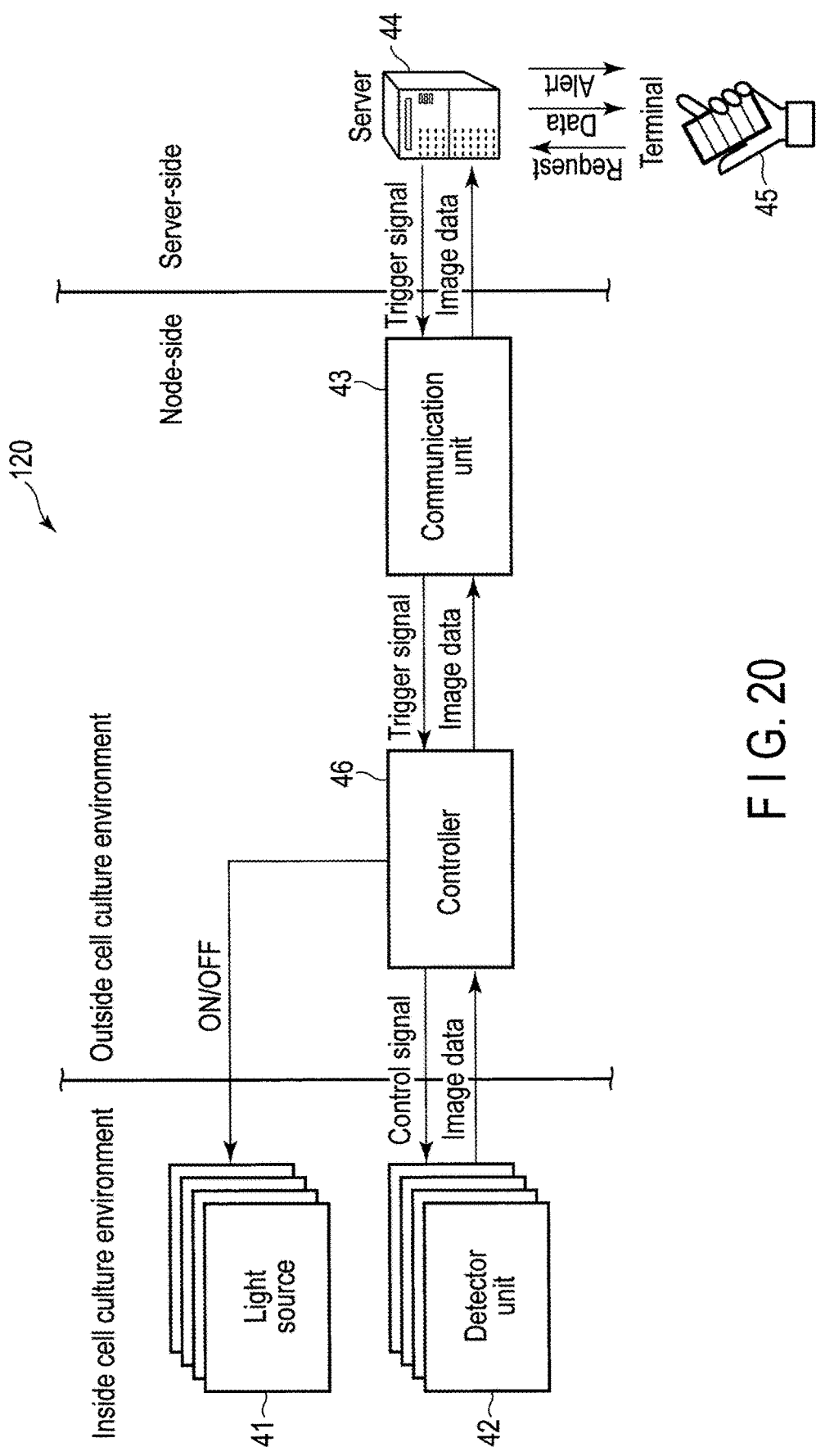
F I G. 20

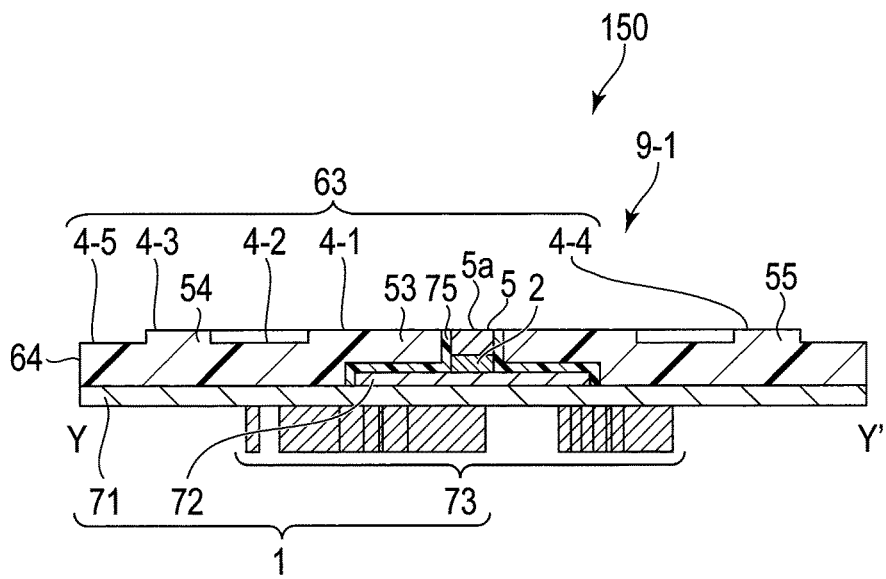
F I G. 25
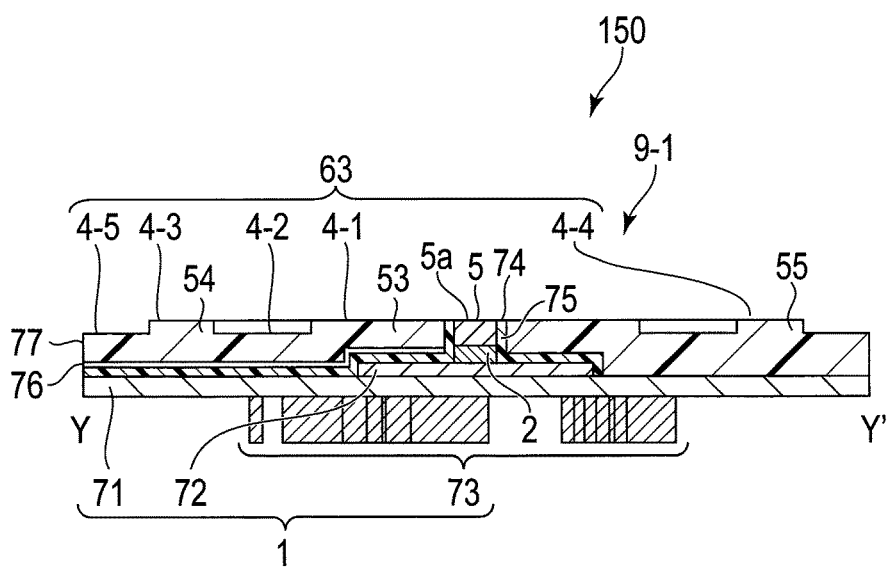
F I G. 26

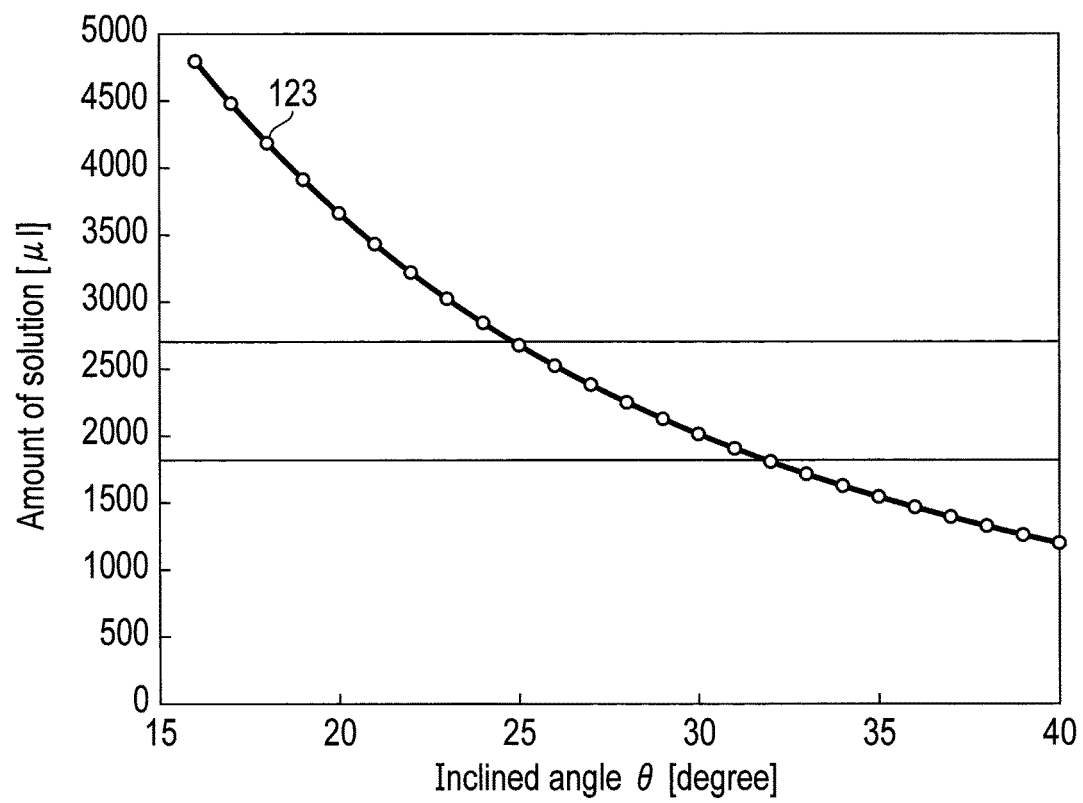
F I G. 31

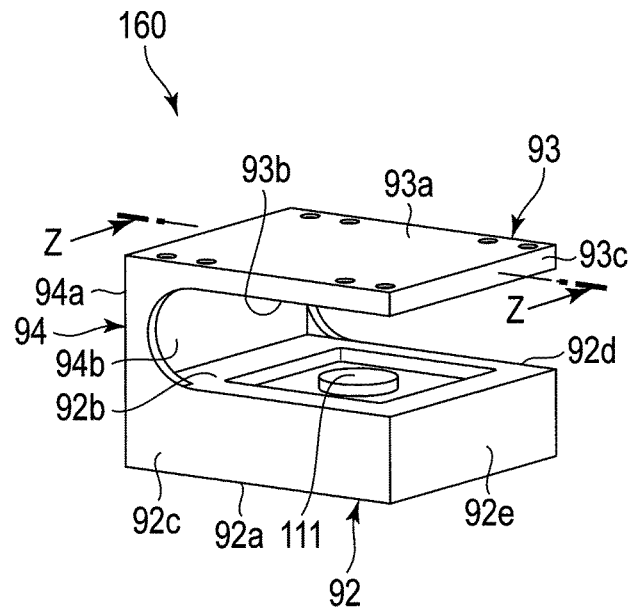
F I G. 32
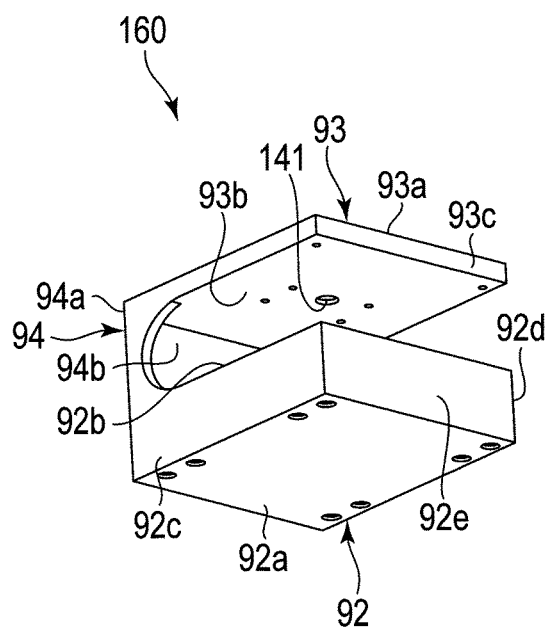
F I G. 33

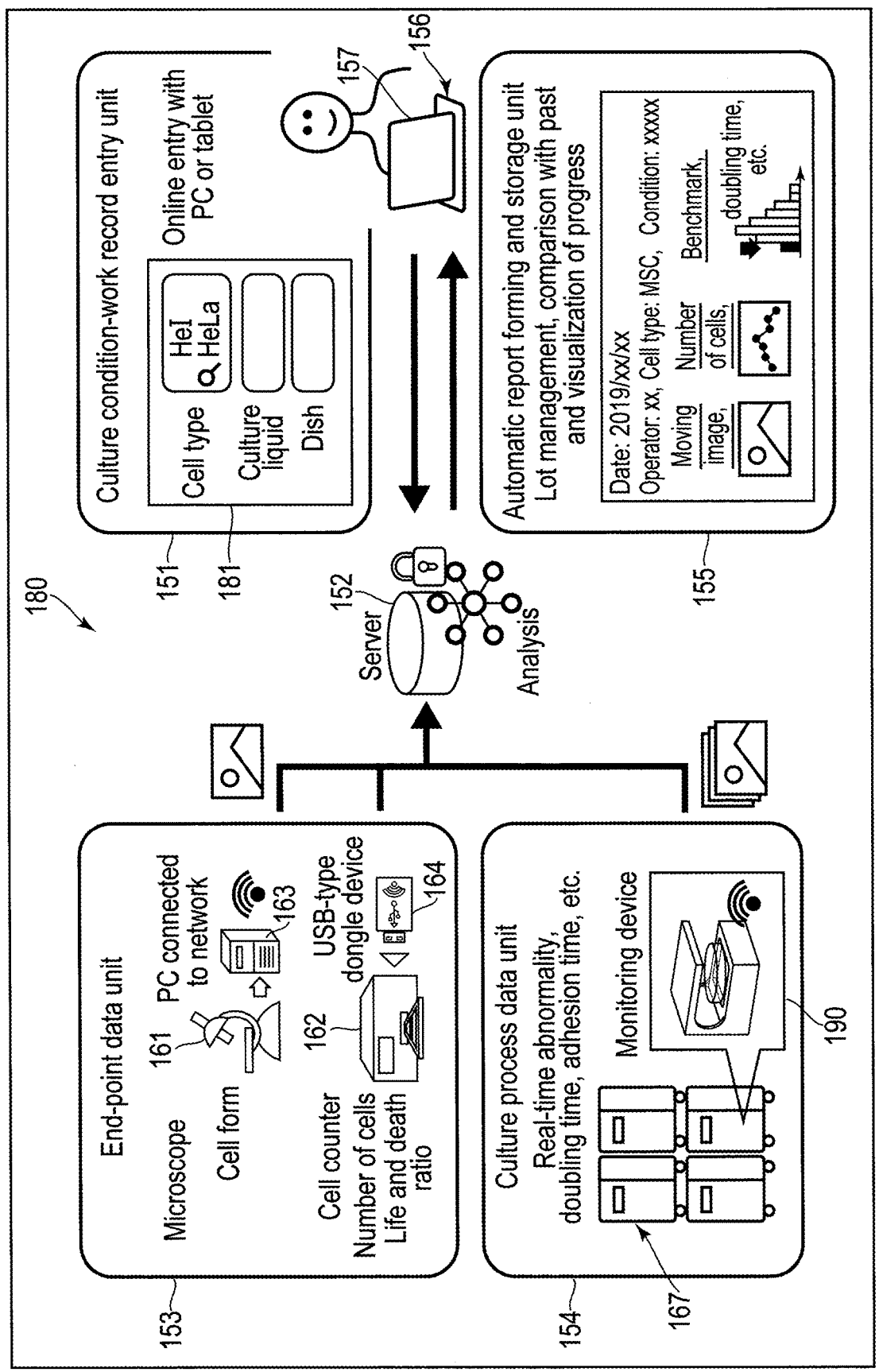
F I G. 36

| | ID:A |
|---|---|
| Culture conditions | Operator: Taro Yamada<br>Cell type: HeLa<br>Generation number: 3<br>Culture container: 10cm dish<br>Coating: collagen<br>Cell culture liquid: DMEM<br>Serum: bovine serum<br>Culture start time and date: 2020/1/3 9:00<br>Culture end time and date: 2020/1/6 9:00 |
| First day | Cell counter<br>  Cell concentration: $2 \times 10^6$ cells/mL<br>  Life and death ratio: 80%<br>  Measurement time: 2020/1/3 8:30 — 191<br>  Comments<br>  [dissemination carried out after 10-fold dilution] |
| Second day | Microscopy <br>  Image capture time: 2020/1/4 9:00 — 192<br>  Comments |
| Fourth day | Microscopy <br>  Image capture time: 2020/1/6 9:00<br>  Cell counter<br>  Cell concentration: $2 \times 10^6$ cells/mL<br>  Life and death ratio: 80%<br>  Measurement time: 2020/1/6 9:30 — 193<br>  Comments |

| | | |
|---|---|---|
| Culture conditions | ID:A<br>Operator: Taro Yamada<br>Cell type: HeLa<br>Generation number: 3<br>Culture container: 10cm dish<br>Coating: collagen<br>Cell culture liquid: DMEM<br>Serum: bovine serum<br>Culture start time and date: 2020/1/3 9:00<br>Culture end time and date: 2020/1/6 9:00 | ID:A<br>Operator: Taro Yamada<br>Cell type: HeLa<br>Generation number: 5<br>Culture container: 10cm dish<br>Coating: collagen<br>Cell culture liquid: DMEM<br>Serum: bovine serum<br>Culture start time and date: 2020/1/9 9:00<br>Culture end time and date: 2020/1/12 9:00 |
| First day | Cell counter<br>  Cell concentration: $2 \times 10^6$ cells/mL<br>  Life and death ratio: 80%<br>  Measurement time: 2020/1/3 8:30<br>Comments<br>  dissemination carried out after 10-fold dilution | Cell counter<br>  Cell concentration: $2 \times 10^6$ cells/mL<br>  Life and death ratio: 80%<br>  Measurement time: 2020/1/9 8:30<br>Comments<br>  dissemination carried out after 10-fold dilution |
| Second day | Microscopy <br>  Image capture time: 2020/1/4 9:00<br>Comments | Microscopy <br>  Image capture time: 2020/1/10 9:00<br>Comments |
| Fourth day | Microscopy <br>  Image capture time: 2020/1/6 9:00<br>Cell counter<br>  Cell concentration: $2 \times 10^6$ cells/mL<br>  Life and death ratio: 80%<br>  Measurement time: 2020/1/6 9:30<br>Comments | Microscopy <br>  Image capture time: 2020/1/6 9:00<br>Cell counter<br>  Cell concentration: $2 \times 10^6$ cells/mL<br>  Life and death ratio: 60%<br>  Measurement time: 2020/1/12 9:30<br>Comments |

MONITORING DEVICE AND MONITORING SYSTEM

CROSS-REFERENCE TO RELATED APPLICATIONS

This application is a Continuation Application of PCT Application No. PCT/JP2020/009864, filed Mar. 6, 2020 and based upon and claiming the benefit of priority from Japanese Patent Application No. 2019-047258, filed Mar. 14, 2019 and U.S. patent application Ser. No. 16/562,798, filed Sep. 6, 2019, the entire contents of all of which are incorporated herein by reference.

FIELD

Embodiments described herein relate generally to a monitoring device and a monitoring system.

BACKGROUND

For observing cells on a culture container (such as a flask, a dish or a multi-well plate), generally, a phase contrast method or a differential interferometry is employed, because in an ordinary bright view field, cells are substantially transparent and poorly visible and a contrast cannot be obtained. However, microscopes, which are used in these methods, require manual techniques including focusing and machine controls therefor. Moreover, they involve large devices (optical systems such as lenses), which are not suitable for being used in parallel and hard to contain in a box for transportation.

For the reason provided above, the phase contrast method and differential interferometry are not suitable for observation of cells placed in, especially, an incubator, a transportation box, a plate of stacked culture plates or the like.

The lens-less imaging method, which observes objects to be measured by bringing the object into contact with a semiconductor optical sensor such as the CMOS image sensor, involves small apparatus as compared to the phase contrast method or the differential interference method because the apparatus does not include an objective lens. Further, with this method, a microscopic observation image of a measuring object can be obtained merely by placing the culturing container, but in many cases, the semiconductor optical sensors easily malfunction, and therefore it is unsuitable for repeated use.

Under these circumstances, there is a demand of a simple monitoring device which can perform monitoring and imaging of cells without a manual operation.

Thus, an object of the embodiments is to obtain a monitoring device which can image microbodies with high viewability.

BRIEF DESCRIPTION OF THE DRAWINGS

FIG. 1 is a cross section schematically showing a structure of a monitoring device according to the first embodiment.

FIG. 2 is a diagram illustrating an operating mechanism of fiber optic plates.

FIG. 5 is a halftone image photograph showing an example of images of cells on an observation screen.

FIG. 6 is a micrograph showing an example of comparative images.

FIG. 16 is a diagram showing the seventh modification of the monitoring device according to the first embodiment.

FIG. 17 is a diagram showing the eighth modification of the monitoring device according to the first embodiment.

FIG. 20 is a block diagram showing a monitoring system according to the second embodiment.

FIG. 25 is a cross sectional view of FIG. 23 taken along line Y-Y'.

FIG. 26 is a diagram illustrating a method of burying a gap with a resin.

FIG. 31 is a graph showing a relationship between an inclined angle θ and a volume V of the solution.

FIG. 32 is a perspective diagram showing the twelfth modified example of the monitoring device of the first embodiment.

FIG. 33 is a perspective view of that shown in FIG. 32 from a different angle.

FIG. 36 is a diagram showing a structure of a monitoring system according to the second embodiment.

FIG. 38 is a diagram showing the first example of a report image.

FIG. 39 is a diagram showing the second example of the report image.

DETAILED DESCRIPTION

Figure 3:
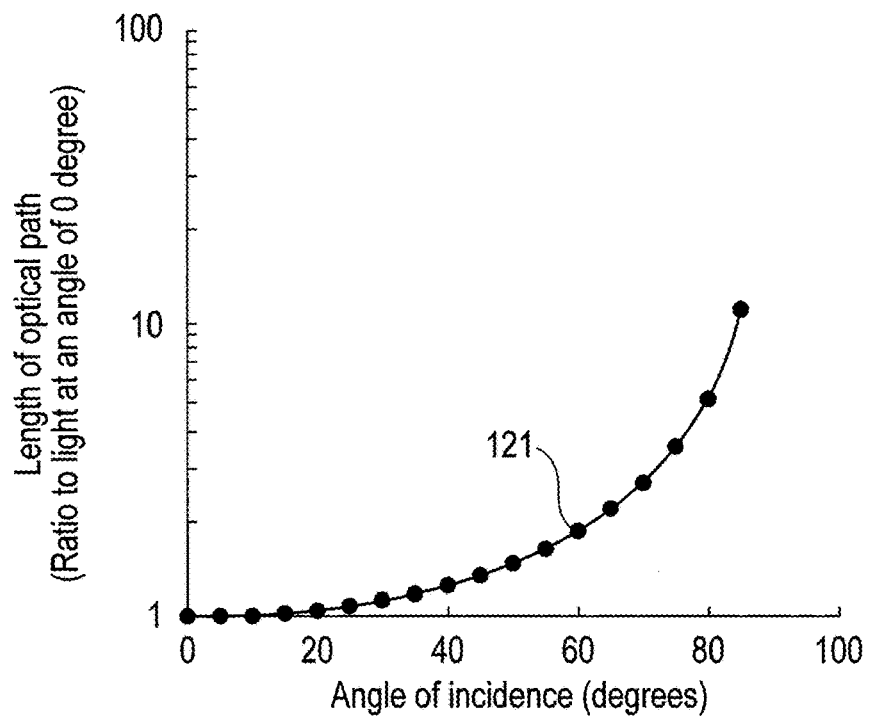
FIG. 3 is a graph chart showing the relationship between the angle of incidence and the length of the optical path in the fiber optic plates.

Various embodiments will be described hereinafter with reference to the accompanying drawings.

In general, according to one embodiment, a monitoring device comprising an image transfer element comprising an incident surface which can receive light from a light-transmissive base material on which a microbody is placed and an emission surface which emits light incident on the incident surface, and a semiconductor optical sensor which receives light from the emission surface.

The image transfer element can transfer two-dimensional image data of a microbody placed on a transparent base material to the semiconductor optical sensor while maintaining high viewability. Here, the transferring can be achieved by, for example, merely loading the microbody in a container including a transparent base material and placing it on the image transfer element, and thus makes it unnecessary to use complicated optical systems or the like. Usable examples of the image transfer element are optical elements such as a fiber optic plate, SELFOC (registered trademark) lens and SELFOC lens array. With the image transfer element, the semiconductor optical sensor can be protected from contacting the base material to prevent damage. Further, when the image transfer element is provided between a microbody and semiconductor optical sensor, the microbody and the semiconductor optical sensor can be distanced away from each other, and therefore the adverse effect on the microbody caused by the heat generated by, for example, the semiconductor optical sensor and the like can be reduced. On the other hand, if the image transfer element is not provided between the microbody and the semiconductor optical sensor placed on the transparent base material, the image may be dim, making it difficult to visually recognize the microbody.

In the case where the image transfer element is a fiber optic plate, the plate filters the light irradiated on the microbody and then further scattered by the microbody in a scattering angular-dependent manner and transmits the light entering the fiber optic plate parallel thereto without being scattered, to the semiconductor optical sensor, thereby obtaining an image with contrast.

Note that the disclosure is merely an example and is not limited by contents described in the embodiments described below. Modification which is easily conceivable by a person of ordinary skill in the art comes within the scope of the disclosure as a matter of course. In order to make the description clearer, the sizes, shapes and the like of the respective parts may be changed and illustrated schematically in the drawings as compared with those in an accurate representation. Constituent elements corresponding to each other in a plurality of drawings are denoted by the same reference numerals and their detailed descriptions may be omitted unless necessary.

FIG. 1 is a cross section schematically showing a structure of a monitoring device according to the first embodiment.

As shown, a monitoring device 10 comprises a detector 9, a light-transmissive container 6 provided on the detector 9 to contain microbodies 7 as a sample to be observed, and a light source 8 provided above the container 6 while opposing the microbodies 7, so as to radiate light on the microbodies 7.

Usable examples of the light source 8 are a point light source, a linear light source, a parallel light source and a planer light source, and preferably, a parallel light source can be used. Examples of the microbodies 7 are cells including a cell of an animal including human, a corpuscle cell, an egg, a sperm, organoid, bacterium and a *bacillus*. Examples other than cells are environmental airborne microbodies such as PM10 and PM2.5, microbeads. The container 6 is light-transmissive, and when accommodating cells as microbodies, for example, a dish, a flask for cell cultures, a multi-well plate, or the like can be employed as the container 6. FIG. 1 shows a dish as an example. The container 6 can contain a culture medium (not shown). Note that the following explanations will be directed to the state that a container is placed on the monitoring device, but the container is not a necessarily essential structural element of the monitoring device.

The detector 9 comprises a semiconductor optical sensor 3 provided on a wiring board 1, a pixel array 2 provided on the semiconductor optical sensor 3, image transfer elements 5 provided on the semiconductor optical sensor 3 via the pixel array 2, and a support member 4. The semiconductor optical sensor 3 used in this embodiment can be electrically connected onto the wiring board 1 by a bonding wire 61. The support member 4 is provided on the wiring board 1 such as to support the pixel array 2, the semiconductor optical sensor 3 and the image transfer elements 5 from side. Examples of the semiconductor optical sensor 3 are a CMOS area sensor, a CCD area sensor and a line sensor.

The image transfer elements 5 each are a device which transfers two-dimensional image data input to an end surface to the other end surface, and in order to observe a microbody contained in the light-transmissive container 6 whose base material of its bottom portion has a thickness of 10 mm or less via the base material of the bottom portion, a fiber optic plate, an SELFOC lens or SELFOC lens array can be used.

As a typical example of the image transfer element 5, the fiber optic plate will now be described.

FIG. 2 is a diagram illustrating a condition of fiber optic plates.

The fiber optic plates 5 are an optical device in which optical fibers are bundled together, and each optical fiber consists of a core 12 and a clad 13. The core 12 has a high refractive index in a central portion where light is transmitted, and the clad 13 covers outer sides of the core 12 and has a low refractive index so as to confine light inside. In the fiber optic plates, parallel light and diffused light are different from each other in transmittance, and therefore these plates have an effect of selectively transmitting the light of a predetermined angle.

As shown, the fiber optic plates 5 include incident surfaces 5a which receive, via the container 6, light rays indicated by arrows 101, 102, 103 and 104 irradiated on cells as the microbodies 7, and emission surfaces 5b which emit the incident light to the semiconductor optical sensor 3. Here, the case where the size of pixels is equal to the diameter R of the fibers is illustrated as an appropriate example. When the diameter R of the fibers is sufficiently minute with respect to the microbody 7, it is not necessarily required that the pixel size and the diameter R of fibers be equal to each other.

Thus, the fiber optic plates used in the embodiment, of the scattering light from the microbody as it is irradiated with light, the light scattered by the microbody is filtered such as to be dependent on scattering angle, and the light entering parallel to the fiber axis of the fiber optic plates without being scattered by the microbody is transmitted to the semiconductor optical sensor. In this manner, an image with contrast can be obtained.

Figure 4:
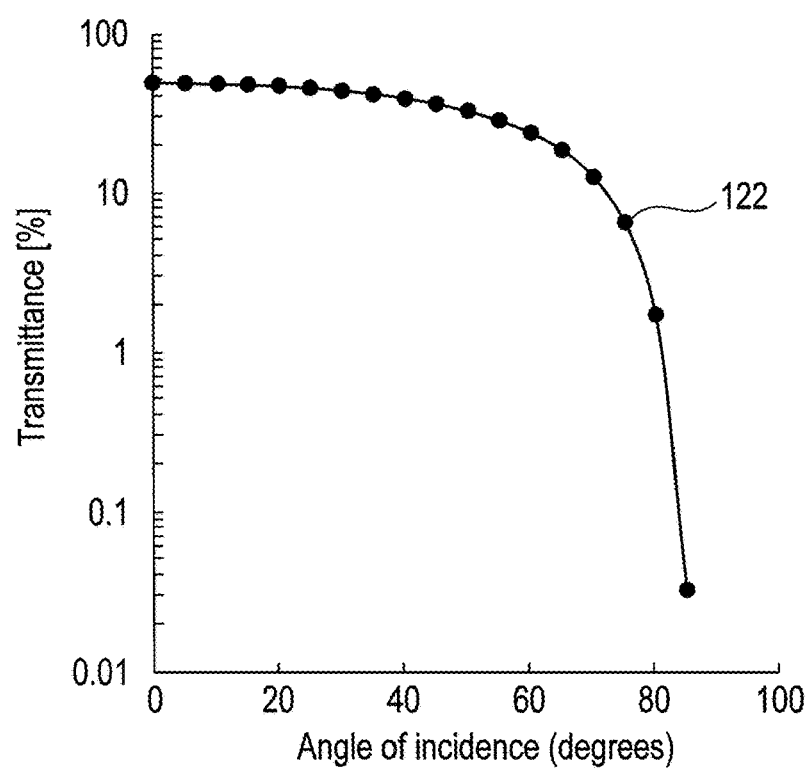
FIG. 4 is a graph chart showing the relationship between the angle of incidence and the transmittance in the fiber optic plates.

FIG. 3 is a graph chart showing the relationship between the angle of incidence on a fiber optic plate and the length of the optical paths. FIG. 4 is a graph chart showing the relationship between the angle of incidence of the fiber optic plate and the transmittance.

The angular-dependent filtering of the fiber optic plate is, as shown by a line 121 in the graph of FIG. 3, carried out by the effect that the length of optical path increases by L/cos ψ to the fiber length L when the angle of incidence is ψ and the attenuation effect when reflecting on an interface between the core and the clad. For example, the length of the optical path of the light at an angle ψ of ±60 degrees is a double to the light at an angle of 0 degree. Here, the length of the optical path contributes exponentially to the transmittance; therefore, as shown by a line 122 in the graph of FIG. 4, when the case of, for example, a transmittance of 50% with respect to the light at an angle of 0 degree is considered, the transmittance to the light at an angle of 60 degrees is greatly attenuated to 25%. Here, for simplicity, the attenuation effect by reflection on the interface between the core and the clad is not considered, and therefore in reality, it is decreased more greatly. Hereafter, the explanation will be provided on an assumption that one threshold angle is 60 degrees.

For example, the light irradiated on the central portion of the cell is transmitted perpendicularly as indicated by an arrow 101, and then emitted to the semiconductor optical sensor 3. The light irradiated onto the vicinity of the center of the cell is concentrated in the center as indicated by an arrow 102, and is emitted to the semiconductor optical sensor 3. The light whose angle ψ with respect to a fiber axis 200 is in a range of ±60 degrees and which is irradiated into an edge portion of the cell is refracted as indicated by an arrow 103, and then attenuated in the fiber optic plates 5. The fiber optic plates can receive light whose angle ψ falls out of a range of ±60 degrees, but it is considered that the most of such light is attenuated. The light irradiated onto the non-cell region is transmitted as it is as indicted by an arrow 104, to reach the semiconductor optical sensor 3.

With the above-described configuration, when a cell is observed via the fiber optic plates 5, the image of the cell shows a bright central portion and a dark edge portion. Thus, an image with contrast made on the outline of the transparent cell can be obtained.

FIG. 5 is a halftone image photograph showing an example of an image of cells on an observation screen, obtained with used of the embodiment.

FIG. 6 is a micrograph showing an example of the image of cells, obtained with a phase-contrast microscope for comparison.

The cells used here were HeLa cells which were treated with paraformaldehyde, and they were contained in a glass bottom dish having a diameter of 35 mm.

As shown in FIG. 5, in the image of the cells, obtained with use of the embodiment, central portions of the cells are shown to be bright and edge portions are dark. Thus, as compared with the phase-contrast microscope photograph of FIG. 6, the contrast of the cells is clearer, thus improving the viewability of the image of the cells.

Moreover, in the observation under microscopes in the phase contrast method and differential interferometry, the focusing or the control of the device therefor is manually carried out. Further, the device is complex since optical parts such as lenses are required. By contrast, with the device according to the embodiment, an image with clear contrast can be obtained merely by receiving the light spotted on the cells, and thus it is no longer unnecessary to manually adjust the image. Furthermore, since the optical parts are not necessary, the structure of the device is simple. Thus, when transparent microbodies such as cells are observed using the monitoring device of the embodiment, an image with clear contrast can be easily obtained at low cost.

Here, based on the Nyquist's theorem, the diameter R of the fibers can be made less than half of the diameter r of microbodies (cells) as indicated by the following formula (A1):

$$R < r/2 \tag{A1}$$

Due to the fact that the size of standard cell species is about 10 μm, in order to identify each individual each cell, the diameter R of the fibers can be set to less than the half thereof, that is, 1 μm to 5 μm, for example, 3 μm. In practice, if the diameter R of the fibers is less than 1 μm, the transmittance of light having a visible wavelength tends to be greatly attenuated, whereas if it exceeds 5 μm, information of 10 μm or less cannot be detected due to the Nyquist's theorem.

The pixel size of the semiconductor optical sensor can be set to less than or equal to the diameter R of the fibers.

In order to attenuate inclined light indicated by the arrow 103 to such an extent as to be able to obtain a contrast, the fiber optic plates need to have a sufficient thickness t. It was experimentally confirmed that an image can be obtained when the thickness t is 2.54 mm. Here, the thickness t is not limited to this, but it can be set to 0.5 mm or greater, 1 mm or greater, or 10 mm or greater according to the necessary contrast or the flatness of the cell species. Note that practically, the thickness t can be set to 1 to 5 mm. If the thickness is less than 1 mm, the effect of angular-dependent filtering becomes small, and it tends to be difficult to obtain the contrast. On the other hands, if it exceeds 1 mm, it exceeds over the loop height of the wire, edge surfaces of the fiber optic plates are formed to be flush with each other and can be brought into contact directly with the container 6. Note that in the case of glassware, the thickness of the bottom of the container 6 employed is 0.2 mm or less, or in the case of plastic, it is about 1 to 2 mm.

As shown in FIG. 1, in the detector 9, the incident surfaces 5a as an edge surface of the fiber optic plates 5 can be flush with an edge surface of a support member 4 on the container 6 side. The incident surfaces 5a of the fiber optic plates 5 can be in close contact with the bottom 6b of the container 6. For example, when the edge portion 4a of the support member 4 is protruded to the container 6 side more than the incident surfaces 5a, an air layer is provided between the incident surfaces 5a and the bottom 6a of the container 6. In this case, refraction and reflection occur in an interface between the container 6 and the air layer having a refractive index deferent from a refract index of the container 6, and in an interface between the air layer and the incident surfaces 5a, respectively. Thus it tends to be difficult to form a clear image in the semiconductor optical sensor 3.

The support member 4 may include an edge portion, in which at least one portion of the edge portion is flushed with the incident surfaces 5a.

Figure 21:
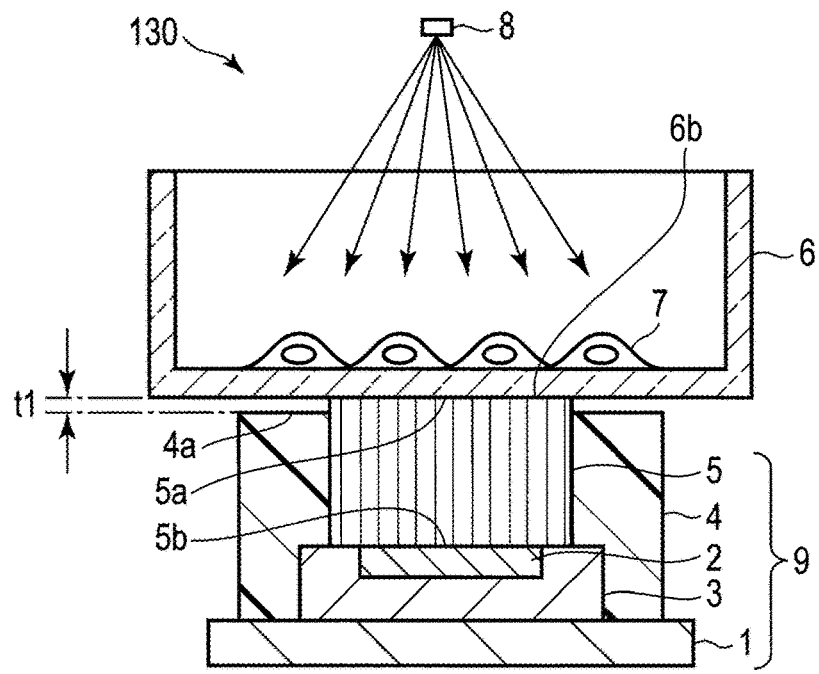
FIG. 21 is a diagram schematically showing a structure of a modification of a detector in a monitoring device according to an embodiment.

FIG. 21 is a diagram schematically showing a configuration of a modification of a detector of a monitoring device according to an embodiment.

As shown in FIG. 21, in a monitoring device 130, the edge portion 4a of the support member 4, which is on a container 6 side is lowered than the incident surfaces 5a of the fiber optic plates 5 to the direction which is parallel to the dejection of the fiber axis of the fiber optic plates 5. Thereby, the incident surface 5a can be protruded to the container 6 side to be in close contact with the bottom 6b of the container 6. In this case, the detection unit 9 entails no drawback optically, but the structural stability is deteriorated, which may possibly cause cracking in the incident surface 5a. The height t1 of the incident surface 5a with respect to the edge portion 4a can be set to 0 mm or more but 1 mm or less.

The monitoring device according to the embodiment is easy to operate for observation and also has a simple structure, and therefore it is possible to observe two or more samples at once.

(Multi-Monitoring Device 1)

Figure 7:
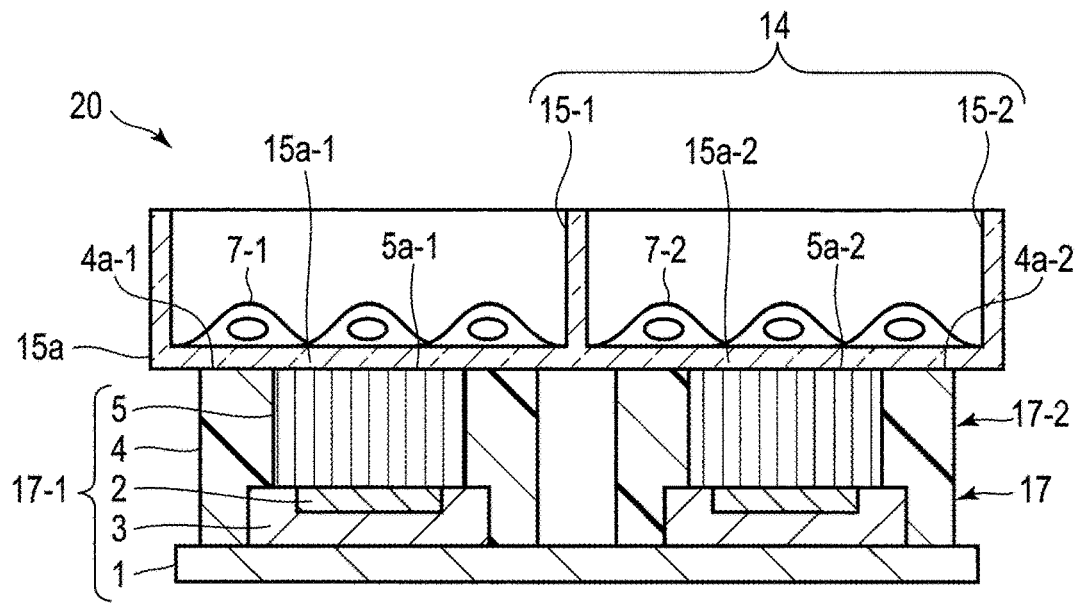
FIG. 7 is a diagram showing the first modification of the monitoring device according to the first embodiment.

FIG. 7 is a diagram showing the first modification of the monitoring device according to the first embodiment, which is a cross section schematically showing an example of a structure of a monitoring device with which two or more samples can be observed.

Figure 8:
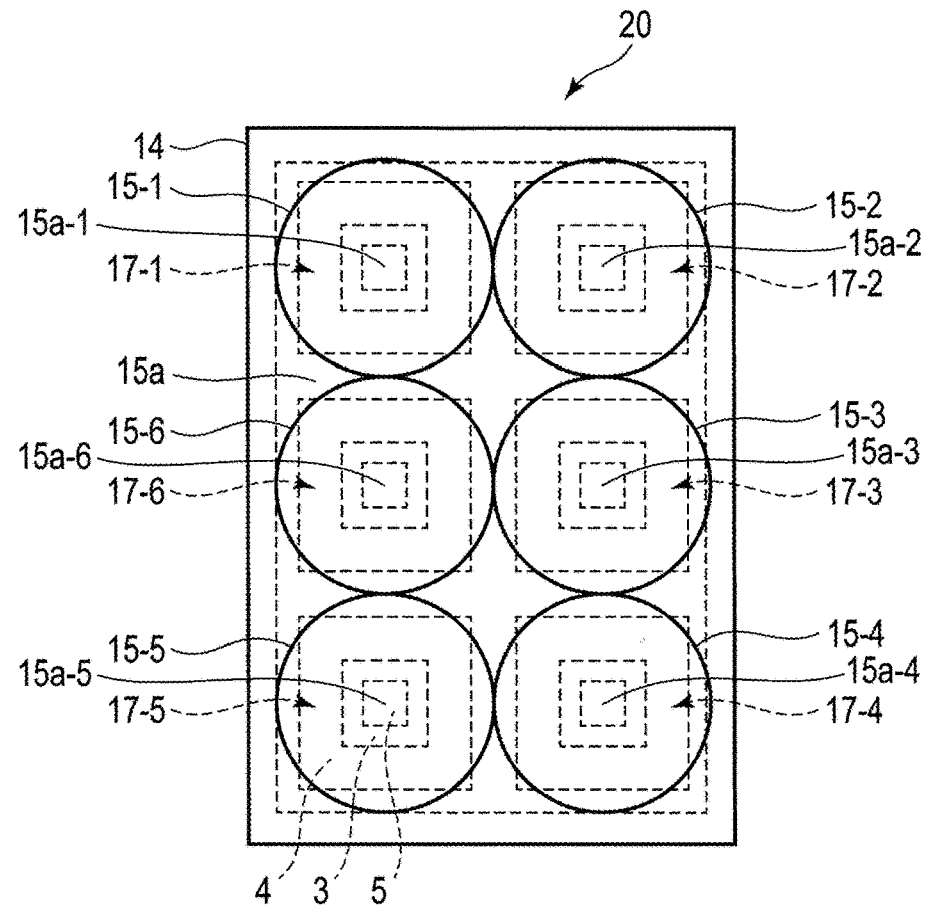
FIG. 8 is a top view of what is shown in FIG. 7 from above.

FIG. 8 is a top view of the device shown in FIG. 7, but the samples are not illustrated.

As shown, a monitoring device 20 is similar to the monitoring device 10 shown in FIG. 1 except for the structures of the container 6 and the detector 9. Here, a multi-well plate 14 comprising a plurality of wells 15-1 and 15-2 which contain a plurality of samples 7-1 and 7-2, respectively, in place of using one container 6. Moreover, in place of one detector 9, a plurality of detectors 17 are used. As the detectors 17, detector members 17-1, 17-2, 17-3, 17-4, 17-5 and 17-6 are provided such as to oppose the wells 15-1, 15-2, 15-3, 15-4, 15-5 and 15-6, respectively. Note that bottom portions 15a-1, 15a-2, 15a-3, 15a-4, 15a-5, and 15a-6 of the respective wells can be divided from each other or they can be integrated as one body of the bottom portion 15a as shown in the FIGS. 7 and 8.

With use of the monitoring device 20, it is possible to observe, for example, a plurality of samples such as samples 7-1 and 7-2 at the same time by arranging the detectors 17-1, 17-2, 17-3, 17-4, 17-5 and 17-6 in parallel.

In detector members 17-1 and 17-2 adjacent to each other, incident surfaces 5a-1 and 5a-2, which are end surfaces of the respective fiber optic plates 5 and end portions 4a-1 and 4a-2 included in the placement portion provided on a multi-well plate 14 side of the support member 4 which supports the fiber optic plate 5 are all made flush with each other.

Figure 9:
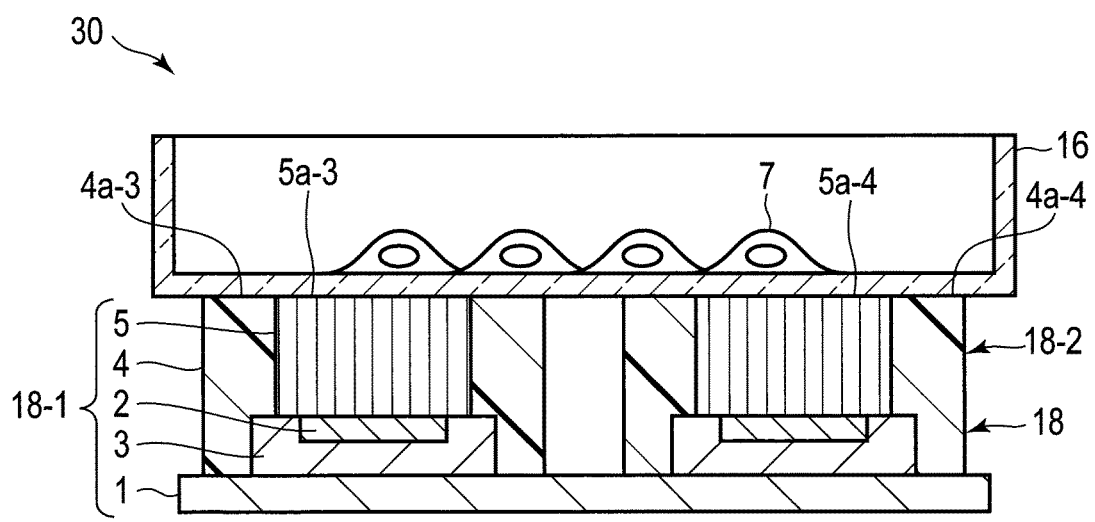
FIG. 9 is a diagram showing the second modification of the monitoring device according to the first embodiment.

FIG. 9 is a diagram showing the second modification of the monitoring device according to the first embodiment, which is a cross section schematically showing another example of the structure of the monitoring device with which samples can be observed by a plurality of detectors.

Figure 10:
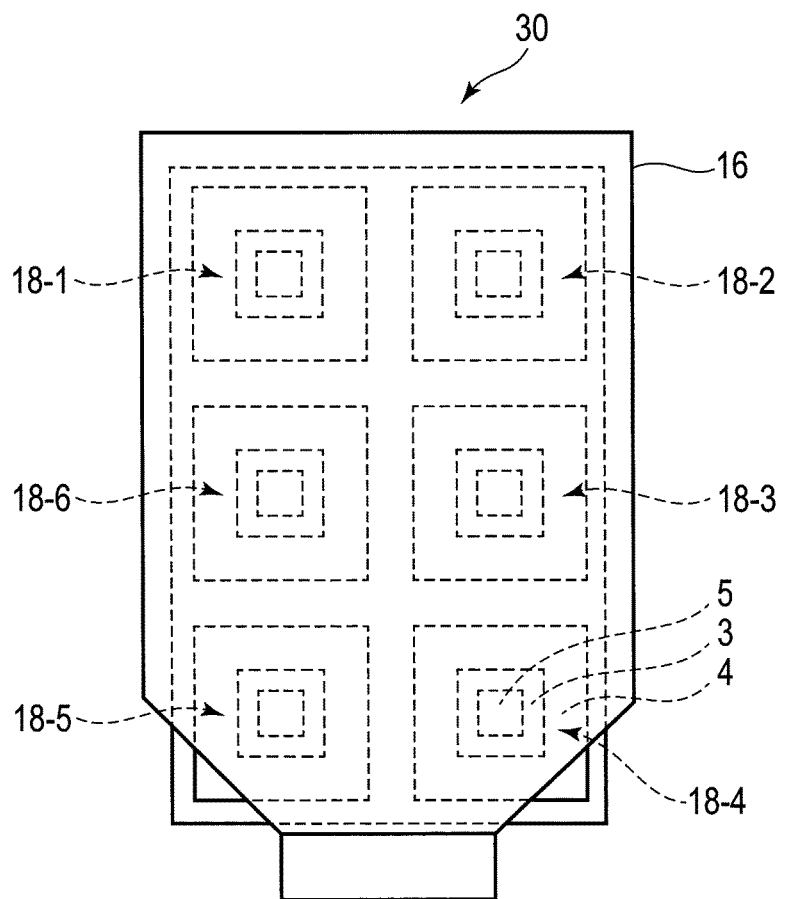
FIG. 10 is a top view of what is shown in FIG. 9 from above.

FIG. 10 is a top view of the device shown in FIG. 9, but the samples are not illustrated.

As shown, a monitoring device 30 has a structure similar to that of FIG. 1 except for the structures of the container 6 and the detector 9. Here, in addition to dishes, a cell-culture flask 16 with a larger size than that of the dishes is used as the container 6. Moreover, in place of one detector 9, a plurality of detectors 18-1, 18-2, 18-3, 18-4, 18-5 and 18-6 are applied to the single cell-culture flask 16.

With use of the monitoring device 30, in which the detectors 18-1, 18-2, 18-3, 18-4, 18-5 and 18-6, which are independent from each other, are provided for various regions of the sample 7, the entire culture container can be covered efficiently, thereby making it possible to observe images with clear contrast and high viewability at the same time.

In detector members 18-1 and 18-2 adjacent to each other, incident surfaces 5a-3 and 5a-4, which are end surfaces of the respective fiber optic plates 5 and end portions 4a-3 and 4a-4 included in the placement portion provided on a cell culturing flask 16 side of the support member 4 which supports the fiber optic plate 5 are all made flush with each other.

(Multi-Monitoring Device 2)

Figure 11:
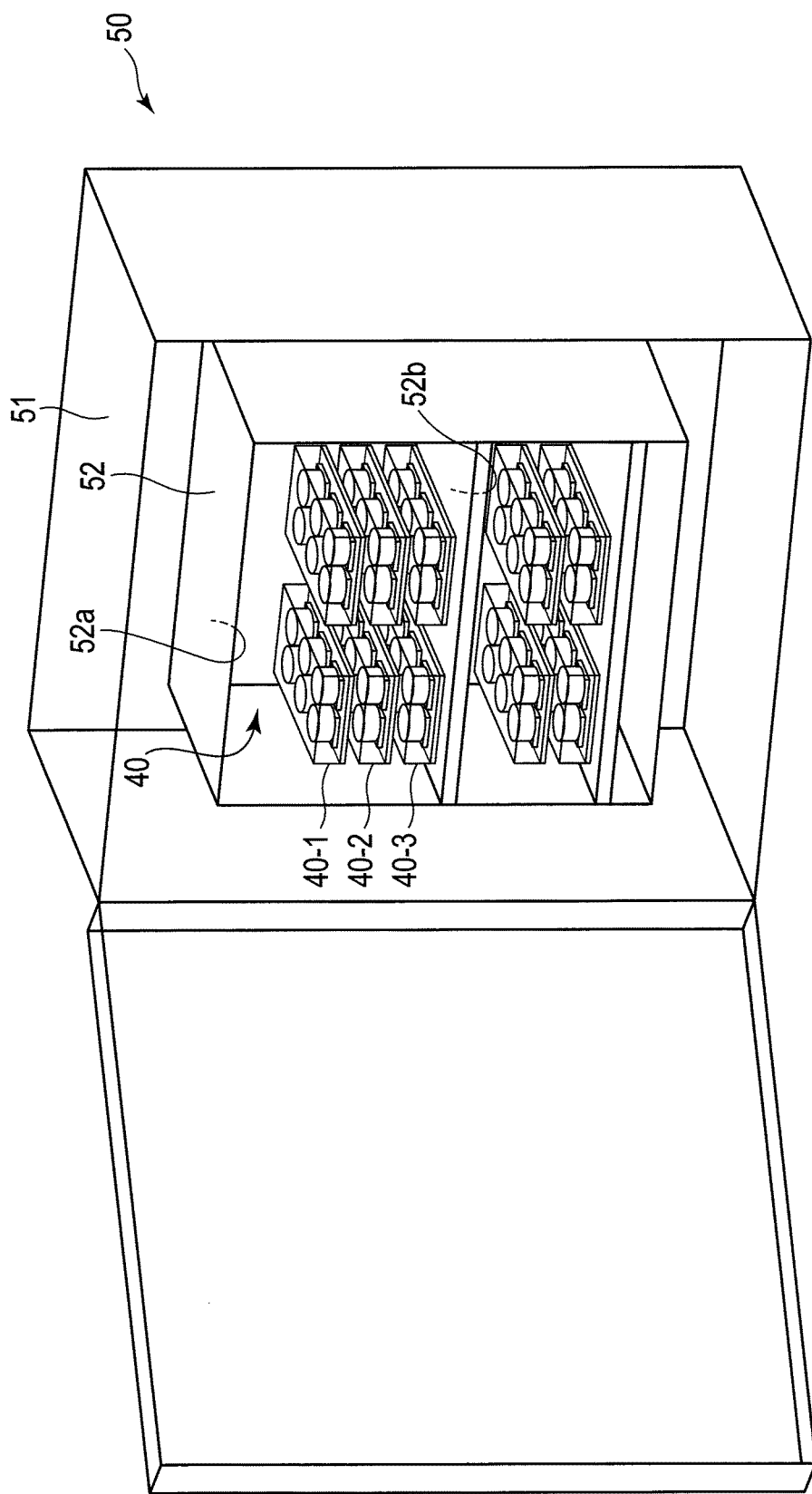
FIG. 11 is a diagram showing the third modification of the monitoring device according to the first embodiment.

FIG. 11 is a diagram showing the third modification of the monitoring device according to the first embodiment, which is a perspective view schematically showing an example of the structure of a monitoring device with which a plurality of samples can be observed while they are stacked one on another.

Figure 12:
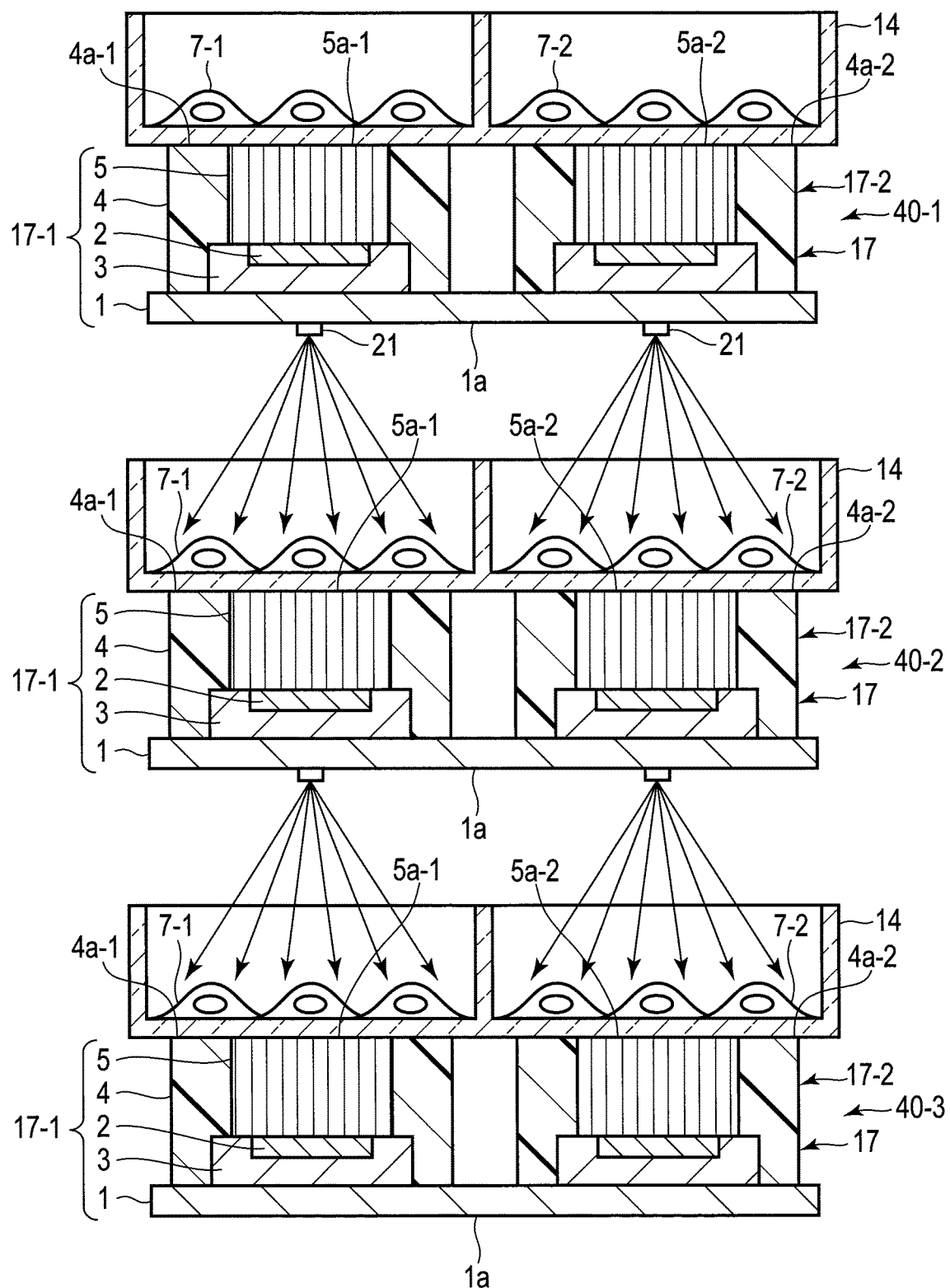
FIG. 12 is a cross section schematically showing a stacked configuration of what is shown in FIG. 11.

FIG. 12 is a cross section schematically showing the stacked structure of what is shown in FIG. 11.

As shown in FIG. 11, a monitoring device 50 comprises, for example, an incubator 51, for example, a two-stage shelves 52 provided in the incubator 51 and a plurality of monitoring units 40 including, for example, three stages of monitoring units 40-1, 40-2 and 40-3 stacked one on another on the stages of the shelves 52.

Moreover, as shown in FIG. 12, each of the monitoring units 40-1, 40-2 and 40-3 comprises a multi-well plate including a plurality of detectors 17 and a plurality of wells provided to oppose the detectors 17, respectively as in the case of the monitoring device 20 shown in FIG. 7. Further, the monitoring units 40 are structured as follows. That is, of the monitoring units 40-1, 40-2 and 40-3, the monitoring units 40-1 and 40-2 other than the lower most monitoring unit 40-3 in the stack, are each provided further with a light source 21 on a surface 1a opposite to the surface on which the semiconductor optical sensor 3 of the substrate 1 is formed, such as to oppose the container 6 of the stage underneath. For example, the light sources 21 of the monitoring units 40-1 and 40-2 each irradiate light onto the monitoring units 40-2 and 40-3 located underneath, respectively. The lowermost monitoring unit 40-3 of the stack has a structure similar to that of the monitoring device 20 shown in FIG. 7 and is not provided with a light source 21 on a surface 1a opposite to the surface on which the semiconductor optical sensor 3 of the substrate 1 is formed. The light source (not shown) which irradiates light on the monitoring units 40-1 is provided in a surface 52a of the shelf board which opposes the multi-well plate 14 of the monitoring units 40-1.

According to the embodiment, in which the monitoring units are stacked on one another and the light source is provided in the substrate located between adjacent monitoring units, it is possible to precisely arrange a more number of monitoring units in such a limited space as an incubator. Thus, with use of the monitoring device 50, it is possible to observe images with clear contrast and high viewability at high operation rate.

In detector members 17-1 and 17-2 adjacent to each other, incident surfaces 5a-1 and 5a-1, which are end surfaces of the respective fiber optic plates 5 and end portions 4a-1 and 4a-2 included in the placement portion provided on a multi-well plate 16 side of the support member 4 which supports the fiber optic plate 5 are all made flush with each other.

(Monitoring Device of Fluorescent Probe)

Figure 13:
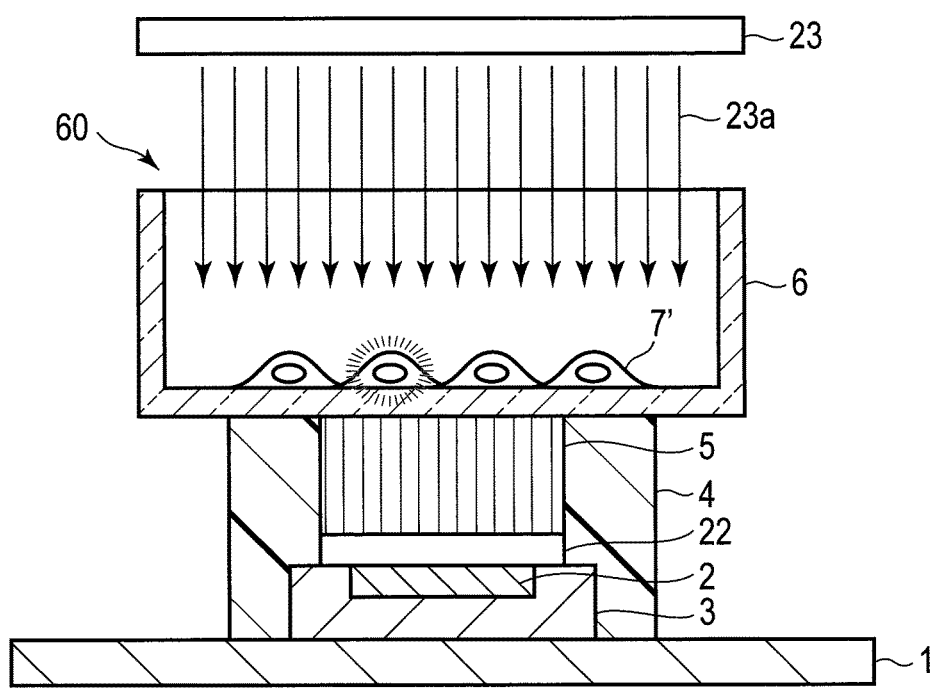
FIG. 13 is a diagram showing the fourth modification of the monitoring device according to the first embodiment.

FIG. 13 is a diagram showing the fourth modification of the monitoring device according to the first embodiment, which is a cross section schematically showing an example of the structure of a monitoring device with which a fluorescent probe which uses fiber optic plates and an optical filter in combination can be observed.

As shown, a monitoring device 60 is provided further with an optical filter 22 between the pixel array 2 and the fiber optic plates 5, which blocks light of a predetermined wavelength. Further, as the light source, a parallel light source 23 is used and as the microbodies, cells 7' in which a fluorescent probe is introduced is used. The monitoring device 60 has a structure similar to that of FIG. 1 except that the light source and the microbodies to be observed are specified and further the optical filter 22 is used.

The monitoring device 60 can irradiate, from the parallel light source 23, substantially parallel excitation light onto the cells 7' in which the fluorescent probe is introduced in advance. When a cell 7' emits light by the excitation light, the emission light enters the fiber optic plates 5. The entering light is allowed to pass the optical filter 22 before emitted to the semiconductor optical sensor 3. As the optical filter 22, a dielectric multilayer film which blocks light of a predetermined wavelength or a light filter containing dyes, pigments or the like can be used.

When using a dielectric multilayer film as the optical filter, it is required that the excitation light be parallel for the angular dependency of the filter, and thus usually, the structure of the optical system is not easy. By contrast, the monitoring device 60, with use of fiber optic plates, can easily improve the parallelism of the excitation light to be blocked, thus relaxing the parallel accuracy required of the irradiated excitation light.

Moreover, when the cells 7' are observed through the fiber optic plates 5 using the monitoring device 60, the central portions thereof are shown bright and the edge portions are dark, thereby achieving clear contrast of the image of those of the cells 7' which emit light, and improving the viewability.

(Monitoring Device Using Reflected Light)

Figure 14:
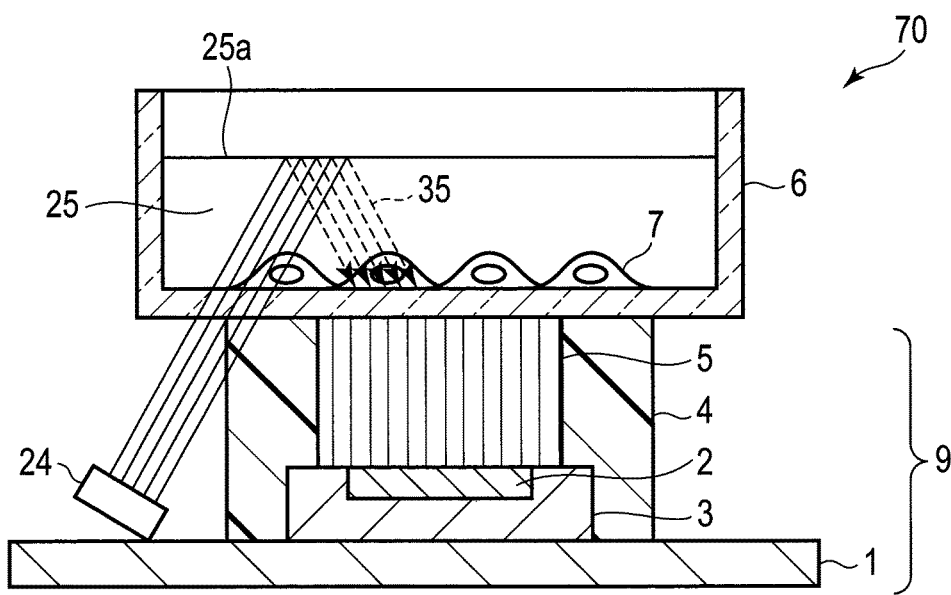
FIG. 14 is a diagram showing the fifth modification of the monitoring device according to the first embodiment.

FIG. 14 is a diagram showing the fifth modification of the monitoring device according to the first embodiment, which is a cross section schematically showing an example of the structure of a monitoring device with which a sample can be observed using reflected light from a light source.

As shown, the monitoring device 70 has a structure similar to that of FIG. 1 except that a light source 24 provided on the substrate 1 is used in place of the light source 8 provided above the container 6. The light source 24 is provided such that reflecting light 35 reflected by a liquid surface 25a of a culture fluid 25 is irradiated on a microbody 7.

With use of the monitoring device 70, the reflection light by the liquid surface 25a exhibit such an effect of substantially illuminating from above the container 6, and clear-contrast images can be easily obtained at low cost as in the case shown in FIG. 1.

The reflectance on the liquid surface is expressed by the following formula (A2):

$$\text{Reflectance } R1 = 2((n0-n1)/(n0+n1))^2 \times 100 \qquad (A2)$$

A refractive index n1 of the culture fluid used here is 1.3 (n1=1.3) and a refractive index n0 of air is 1.0 (n0=1.0); therefore if these values are substituted into the equation, a reflectance on the liquid surface of 1.7% can be obtained.

Figure 15:
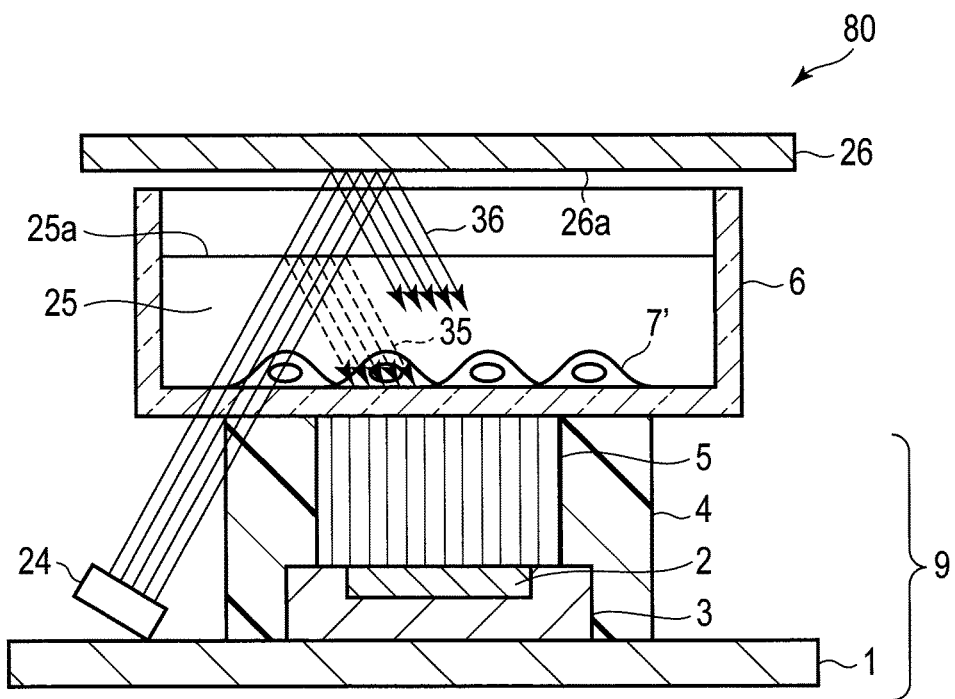
FIG. 15 is a diagram showing the sixth modification of the monitoring device according to the first embodiment.

FIG. 15 is a diagram showing the sixth modification of the monitoring device according to the first embodiment, which is a cross section schematically showing another example of the structure of a monitoring device with which a sample can be observed using reflected light from a light source.

As shown, a monitoring device 80 has a structure similar to that of FIG. 14 except that a reflector 26 is provided above the container 6. With the passive reflector 26 thus placed, reflected light 36 reflected by a reflector surface 26a can be further irradiated onto the microbodies 7 to enhance the efficiency of reflected light to 90% or higher, thus making it possible to easily obtain images with clear contrast and sufficient viewability at low cost.

Moreover, in the monitoring devices 70 and 80, a light source is provided in the substrate 1 of the same detector 9. With this structure, even if containers of different formats are mixedly loaded for incubation, they can be easily managed. Thus, it becomes also possible to conduct different culture experiments in parallel within the same incubator.

(Sample-Scannable Monitoring Device)

FIG. 16 is a diagram showing the seventh modification of the monitoring device according to the first embodiment, which is a cross section schematically showing an example of the structure of a monitoring device with which a sample can be observed while scanning it.

As shown, a monitoring device 90 has a structure similar to that of FIG. 1 except that it further comprises a horizontal drive mechanism 27 attached to the substrate 1 and supporting the detector 9 so as to be horizontally movable.

With use of the monitoring device 90, samples can be observed while scanning them because the detector 9 underneath the container 6 is horizontally movable. Therefore, as in the case of FIG. 1, it is possible to easily obtain images with clear contrast at low cost.

FIG. 17 is a diagram showing the eighth modification of the monitoring device according to the first embodiment, which is a cross section schematically showing another example of the structure of a monitoring device with which samples can be observed while scanning them.

As shown, a monitoring device 100 has a structure similar to that of FIG. 1 except for the structures of the fiber optic plates 5 and the detector 9, and that it further comprises a horizontal drive mechanism 28 which supports a detector to be horizontally movable. Here, the fiber optic plates 5 are fixed to the bottom portion of the container 6. Further, in place of the detector 9, a detector 9' is used, which includes a semiconductor optical sensor 3 connected onto the wiring board 1 by the bonding wire 11, a pixel array 2 provided on the semiconductor optical sensor 3, and a pair of support members 4 which support the semiconductor optical sensor 3 and the pixel array 2 from sides.

With use of the monitoring device 100, samples can be observed while scanning them because the detector 9' underneath the fiber optic plates 5 attached to the container 6 is horizontally movable. Therefore, as in the case of FIG. 1, it is possible to easily obtain images with clear contrast and high viewability at low cost. Note that in the above-described cases, the detectors 9 and 9' are moved, but it is also possible to horizontally move the container 6. As the semiconductor optical sensor, not only an array sensor but also a line sensor can be used.

(Monitoring Device which Detects Forward Scattering Light and Sideward Scattering Light)

Figure 18:
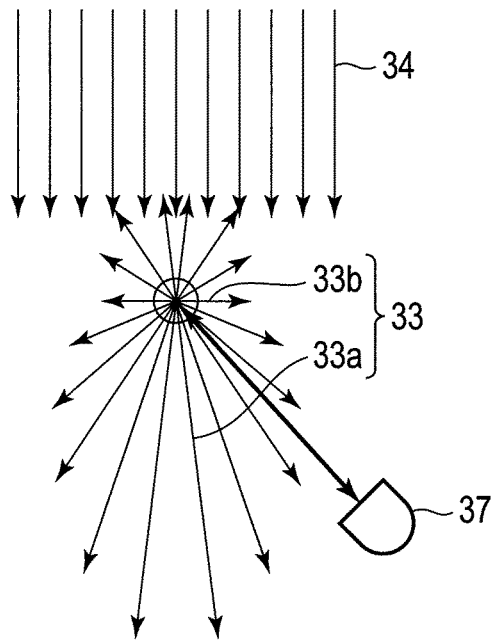
FIG. 18 is a diagram illustrating a condition of a microbody and scattering light.

FIG. 18 is a diagram illustrating a condition of a microbody and scattering light.

As shown, for example, in a microbody such as cell containing a microstructure therewithin, scattering light 33 is generated from irradiated light 34. Of the scattering light 33, forward scattering (FSC) 33a is known as a parameter indicating the size of the cell, and sideward scattering (SSC) 33b is known as a parameter indicating the complexity of the internal structure. According to the required data, a respective type of scattering light can be detected by a detector 37.

Figure 19:
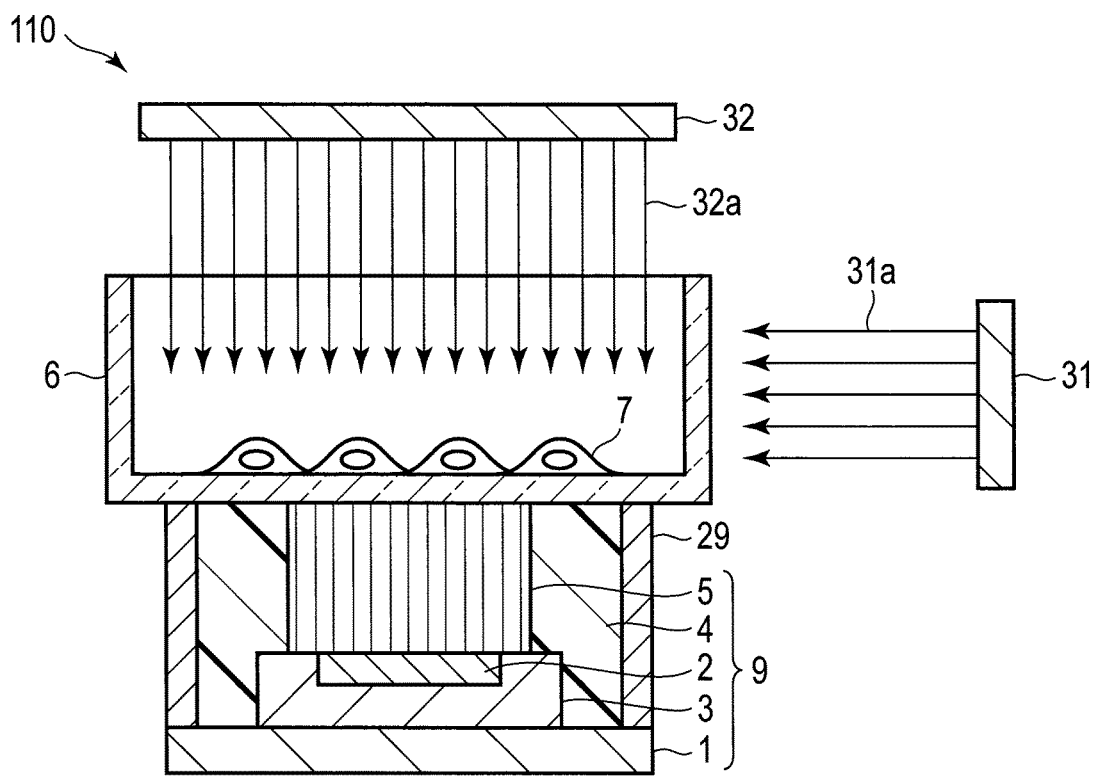
FIG. 19 is a diagram showing the ninth modification of the monitoring device according to the first embodiment.

FIG. 19 is a diagram showing the ninth modification of the monitoring device according to the first embodiment, which is a cross section schematically showing a monitoring device which detects forward scattering light and sideward scattering light.

As shown, a monitoring device 110 has a structure similar to that of FIG. 1 except for the structure of the light source 8 and that it further comprises a light-shielding plate 29 which shields light around the detector 9. The monitoring device 110 comprises, in place of the light source 8, a vertical illumination light source 32 for measuring the FSC and a horizontal illumination light source 31 for measuring the SSC.

With use of the monitoring device 110, the vertical illuminator light source 32 irradiates vertical light 32a and the horizontal illumination light source 31 irradiates horizontal light 31a both in a sequential manner to measure FSC and SSC, respectively. With these measurements, images with clear contrast and high viewability can be easily obtained at low cost.

As the container 6, for example, a light-transmissive member such as polystyrene or glass is used. Note that the light may be irradiated at an angle except for perpendicular or horizontal. The irradiation angular direction of the first light source may be set to a first angle with respect the fiber axis of the fiber optic plates, which is, for example, 0 degree, and the irradiation angular direction of the second light source can be set to a second angle which is different from the first angle, for example, 90 degrees. Thus, the scattering light which enters at an angle in a range of ±60 degrees with respect to the fiber axis of the fiber optic plates can be measured. Note that the edge surfaces of the fiber optic plates 5 and the semiconductor optical sensor 3 should preferably be light-shielded. In place of providing the light-shielding plate 29, a black member may be used as the support member 4.

(Shape 1 of Support Member of Detector)

Figure 22:
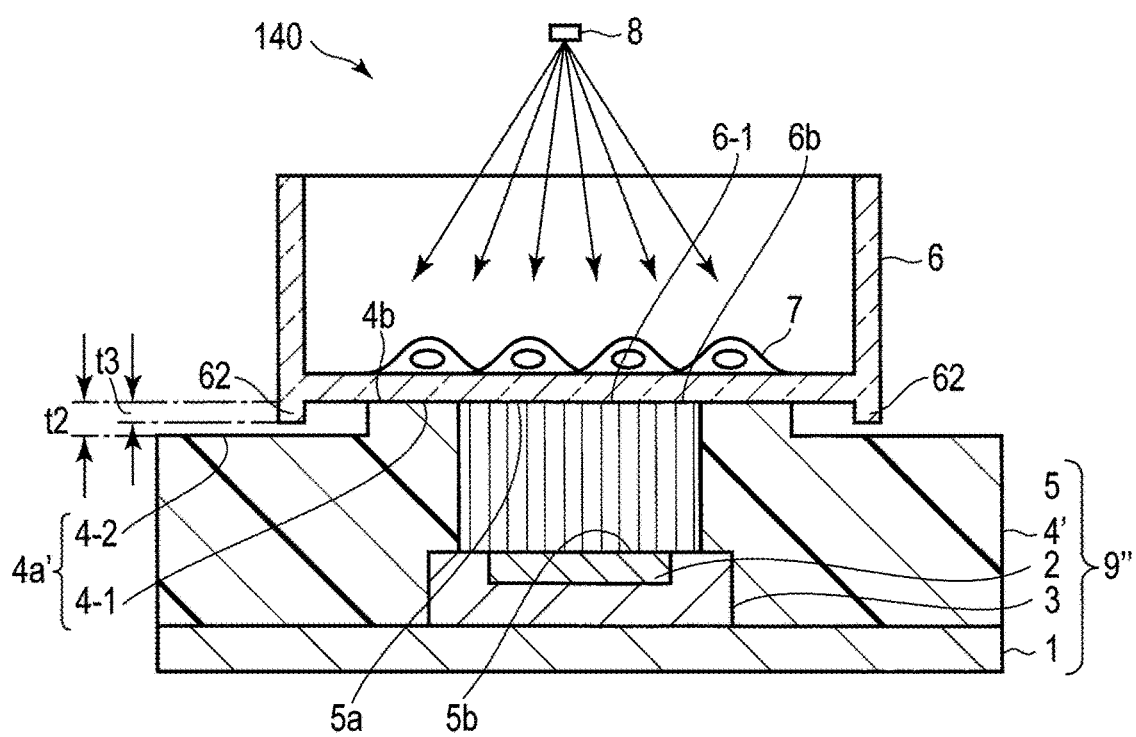
FIG. 22 is a diagram schematically showing a structure of another modification of a detector in a monitoring device according to an embodiment.

FIG. 22 shows the tenth modified example of the monitoring device according to the embodiment, which is a cross section schematically showing the structure of the support member of the monitoring device according to the embodiment.

As shown, the container 6 may include a leg 62 provided on a bottom 6b. In such a case, as shown in a detector 9" of a monitoring device 140, a support member 4' used here is formed to include a step in an end portion 4a' on a container 6 side. In the end portion 4a', an end portion member 4-1 located around the fiber optic plate 5 can be flush with the incident surface 5a. Thus, the incident surface 5a of the fiber optic plate 5 and the end portion member 4-1 of the support member 4 can be brought into tight contact with a region 6-1 of the bottom 6b of the container 6. On the other hand, an end portion member 4-2 located around the end portion member 4-1 of the support member 4 can be lowered from the end portion member 4-1 by a distance t2 in a direction parallel to a fiber axis of the fiber optic plate 5. The distance t2 can be increased greater than the height t3 of the leg 62. With this structure, in the monitoring device 140, even if the container 6 is provided with the leg 62, it is difficult to become contact the end portion member 4-2 of the support member 4. The height of the leg t3 of the container 6 can be set to 0.1 to 3.0 mm. The distance t2 can be set to 0.1 to 5.0 mm. The monitoring device 140 has a structure similar to that of FIG. 1 except that the step is provided in the end portion 4a'. Note that a part of the support member 4 which faces the bottom 6b of the container 6 is referred to a placement portion as the end portion member 4-1.

(Shape 2 of Support Member of Detector)

Figure 23:
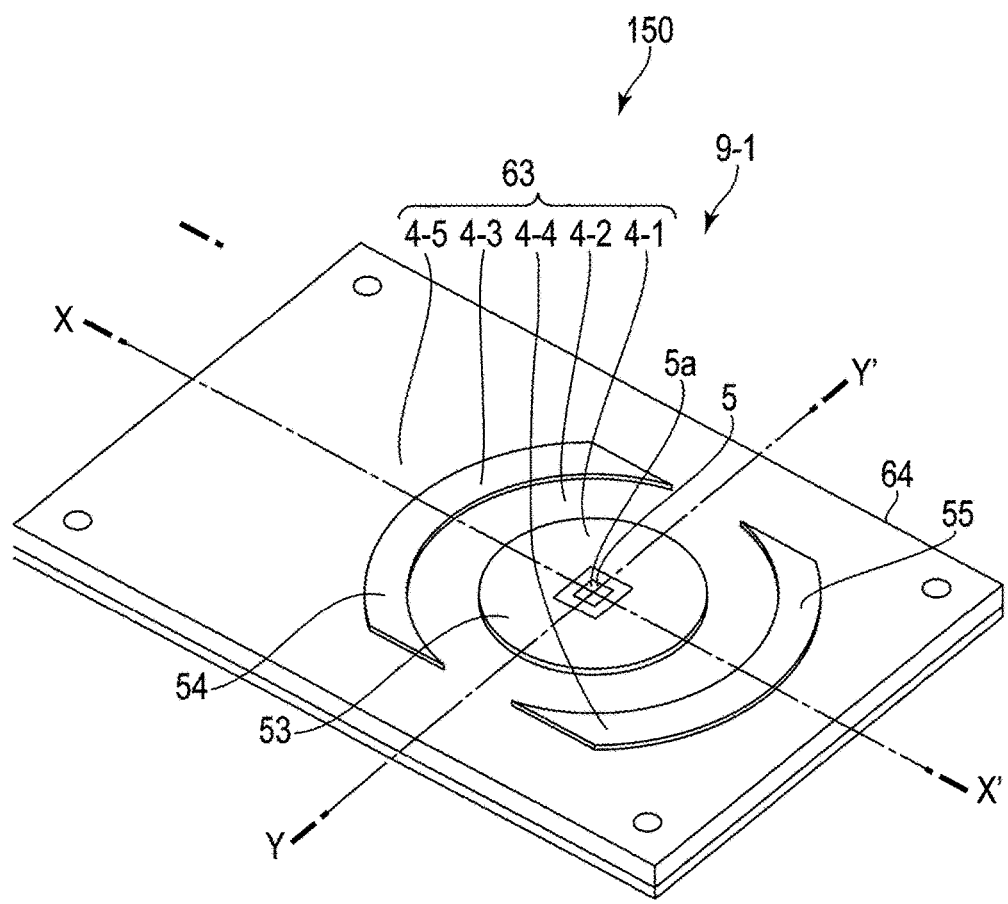
FIG. 23 is a perspective diagram showing an example of the detector of the monitoring device according to the embodiment.

FIG. 23 shows a perspective diagram of the detector of the eleventh modified example of the monitoring device according to the first embodiment.

Figure 24:
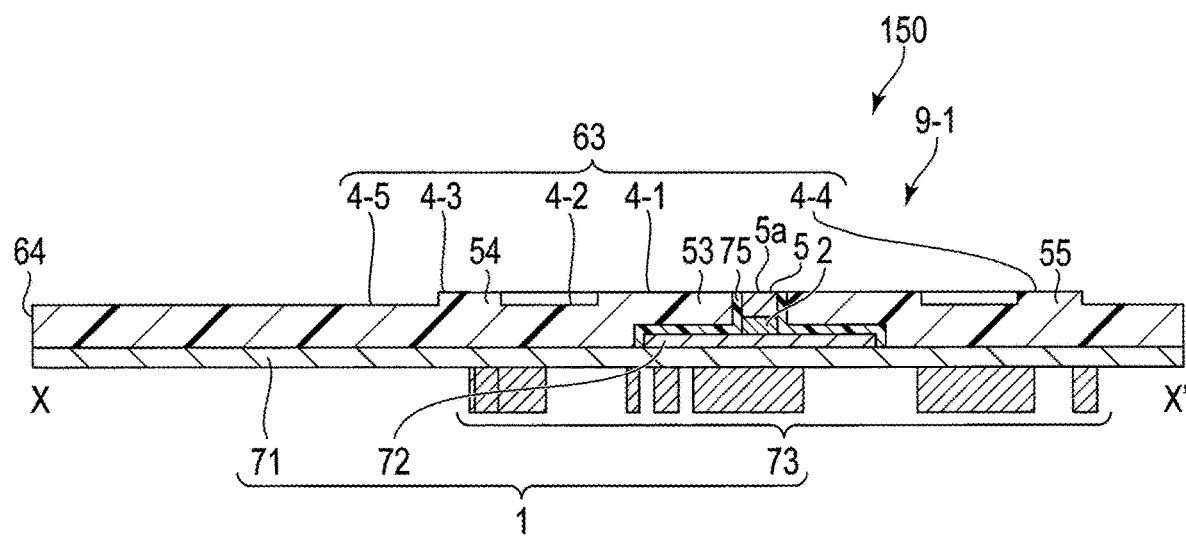
FIG. 24 is a cross sectional view of FIG. 23 taken along line X-X'.

FIG. 24 is a cross section of that of FIG. 23 taken along line X-X'.

FIG. 25 is a cross section of that of FIG. 23 taken along line Y-Y'.

As shown in FIGS. 24 and 25, the monitoring device 150 includes a detector member 9-1, and the detector 9-1 includes a CMOS sensor 2 provided on a second substrate 72 of the wiring board 1, a pixel array (not shown) provided on the CMOS sensor 2, a fiber optic plate 5 provided on the CMOS sensor 2 via the pixel array and a support member 64 supporting the fiber optic plate 5.

The support member 64 is another example of the support member 4' shown in FIG. 22, and the shape of the placement portion is different from the shape of the placement portion of the support member 4'. As shown in FIGS. 23, 24 and 25, the support member 64 includes, on a placement portion side, a first projecting portion 53 including a first circular end portion member 4-1 provided to enclose the surroundings around the incident surface 5a of the fiber optic plate 5 as a center thereof, and at least part of which is flush with the incident surface 5a, a second projecting portion 54 including a semicircular ring-shaped second end portion member 4-3, at least part of which is flush with the incident surface 5a, and a third projecting portion 55 including a semicircular ring-shaped third end portion member 4-4 opposing the second projecting portion 54 via the first projecting portion 53 and spaced apart from the first projecting portion 53, at least part of which is flush with the incident surface 5a. Between a pair of the first end portion member 4-1 and the second end portion member 4-3, a pair of the first end portion member 4-1 and the third end portion member 4-4 and a pair of the second end portion member 4-3 and the third end portion member 4-4, there is provided a fourth end portion member 4-2 lowered from the first end portion member 4-1, the second end portion member 4-3 and the third end portion member 4-4 by a predetermined distance in a direction parallel to a fiber axis of the fiber optic plate 5. On an outer side of the second end portion member 4-3 and the third end portion member 4-4, there is provided a fifth end portion member 4-5 lowered from the second end portion member 4-3 and the third end portion member 4-4 by a predetermined distance in a direction parallel to the fiber axis of the fiber optic plate 5. The end portion members 4-1, 4-3, 4-4, 4-2 and 4-5 constitute an end portion 63 of the support member 64. The predetermined distance can be set greater than the length of the leg of the container used for observation.

The wiring board 1 includes a first printed circuit board 71, a second substrate 72 provided on one main surface of the first printed circuit board 71, and parts 73 such as an IC, capacitor a connector and the like, provided on the other main surface of the first printed circuit board 71.

The fourth end portion member 4-2 is lowered further from the first end portion member 4-1, the second end portion member 4-3 and the third end portion member 4-4.

With this structure, for example, as in the case of the monitoring device shown in FIG. 22, a projecting portion of the leg of the container used for observation is allowed to escape on the fourth end portion member 4-2, and thus the bottom portion of the container can be brought into sufficiently tight contact with the incident surface 5a of the fiber optic plate 5 and the first end portion member 4-1. Further, in the case of the monitoring device including a detector 9-1, the second projecting portion 54 and the third projecting portion 55 is provided, in addition to the first projecting portion 53, on a placement portion side of the support member 64. With this structure, when the size of the bottom of the container employed is sufficiently larger as compared to, for example, the size of the bottom of the container shown in FIG. 22, the projection structure of the leg of the container is allowed to escape on the end portion member 4-5, which is lowered further from the second end portion member 4-3 and the third end portion member 4-4, and thus the bottom portion of the container can be brought into sufficiently tight contact with the incident surface 5a of the fiber optic plate 5 and the first end portion member 4-1. Moreover, at this time, the bottom portion of the container can be supported by the first end portion member 4-1, the second end portion member 4-3 and the third end portion member 4-4, the container can be placed more stably as compared to the case where it is supported by the first end portion member 4-1 only, for the observation.

When containers of different sizes are used, for example, a dish having an outer diameter of 35 mm, a dish having an outer diameter of 60 mm and a dish having an outer diameter of 90 mm, the dimensions of the end portion 63 are set as a diameter of the first end portion member 4-1 being 20 to 30 mm, a width of the end portion member 4-2 being 5 to 20 mm, and widths of the second end portion member 4-3 and the third end portion member 4-4 being 5 to 20 mm. Thus, dishes of any size can be placed stably on the placement portions. Further, when the dimensions of the end portion 63 are of such values as set out above, other usable examples of the container are, for example, flasks of sizes of T12.5, T25 and T75.

Further, a gap 74 between the first projecting portion 53 and the fiber optic plate 5 can be buried with a resin 75. Thus, malfunction of the CMOS sensor 2 and the parts 73, which may be caused by the solution or like leaking from the container, can be prevented.

FIG. 26 is a diagram illustrating an example of the method of burying the gap with a resin.

This figure is similar to FIG. 25 except that an injection hole 76 is provided from a side surface 77 of the support member 64 over to the gap 74. As shown, the gap 74 can be buried with the resin 75 by injecting the resin from the injection hole 76. An upper surface of the resin 75 can be make flush with the fiber optic plate 5.

Examples of such a resin are thermosetting resins such as epoxy resin and silicone resin, thermosetting resin such as polystyrene, acrylonitrile butadiene styrene resin, and hot-melt adhesive.

Note that the support member 64 of the monitoring device 150 is provided with three projecting portions 53, 54 and 55, but there may be four or more projecting portions provided.

(Material of Support Member of the Monitoring Device)

For example, when replacing a culture fluid without moving a cell culturing container on the semiconductor optical sensor from its position, the experimenter unloads the monitoring device from the $CO_2$ incubator while leaving the culture container on the placement portion and carries it to a clean bench. During this period, if the culture container needs to be fixed to a device using a fixing tool or the like, the workability is degraded since it will require a removal process as well.

Therefore, in the monitoring device of the embodiment, such a region is formed on the placement portion that the container does not easily slip on. Thus, the positional relationship between the semiconductor optical sensor and the container can be easily maintained without using a fixing tool or the like.

In order to obtain such a region, a material on which the container cannot easily slip may be used. This material can be used for at least a part of the placement portion of the support member or for the entire support member.

Here, it is desirable that a static frictional force acts on this material at an angle greater than at least such an angle that the culture fluid in the culture container overflows when inclined. In other words, the friction angle G0 needs to be greater than the angle at which the culture fluid spills. Further, this material can be selected based on the measurement in static frictional force between the container and the material used as the support member.

Figure 27:
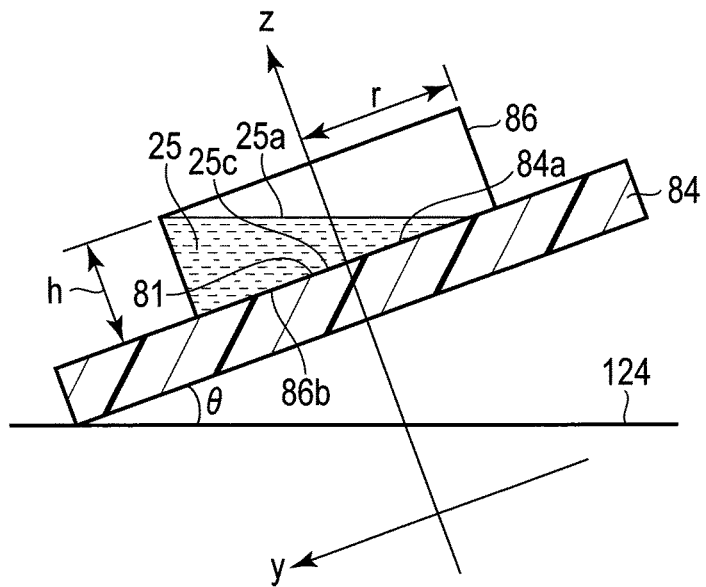
FIG. 27 is a schematic diagram illustrating the static frictional force utilized in the embodiment.

FIG. 27 is a schematic diagram illustrating a method used for measuring the static frictional force in the embodiment.

This schematic diagram shows a situation in which a container 86 with a circular bottom portion 86b contains a microbody and a solution containing the microbody, that is, for example, a culture solution 25, and a board 84 to be used as the support member is inclined at an angle θ greater than the angle that the solution 25 in the container 86 overflows. The arrows y and z indicate directions which pass through the center of the bottom portion 86b of the container 86 and normal to each other. The arrow y is a direction inclined along the bottom portion 86b. The arrow z is a direction perpendicular to the bottom portion 86b. The figure also indicates a surface 25a of the solution and a bottom 25c of the solution.

A static frictional force p acts on a contact surface 81 between the bottom 86b of the container and a placement portion-side end surface 84a of the board 84 of the support member. The frictional angle is defined as an angle at which the container 86 starts to slide on the board 84 of the support member.

The relationship between the frictional angle G0 and the static friction coefficient μ is expressed by Formula (1).

$$\mu = \tan\theta 0 \tag{1}$$

It is known in terms of physics that the relationship is not dependent on a macroscopic shape of the container 86, but determined based on the material of the container 86 and the material of the board 84 of the support member.

The following formula (2) is an example of the formula to obtain the inclining angle θ for the solution 25 to spill.

When V represents the volume of the solution in the container, h represents the height of the container and r represents the inner diameter thereof, the volume V is represented in the following formula (2).

$$V = r^3 \tan\theta \left( -\frac{\sin^3 \alpha}{3} + \sin\alpha - \alpha\cos\alpha \right) \tag{2}$$

Further, α in the formula (2) is represented by the following formula (3).

$$\alpha = \cos^{-1}\left(-\frac{l-r}{r}\right) \tag{3}$$

A process to induce the formula (2) will now be described.

Figure 28:
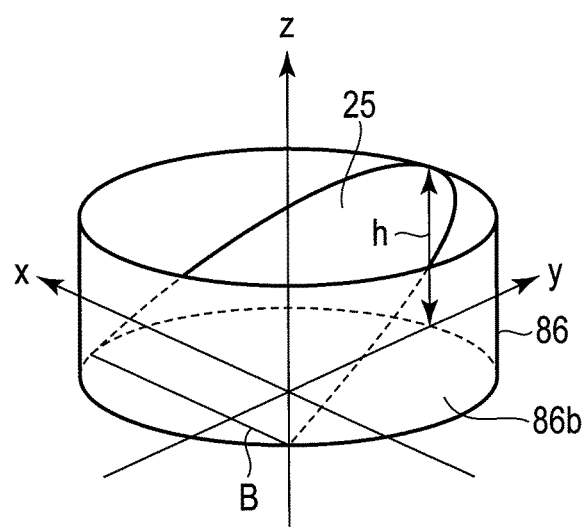
FIG. 28 is a perspective diagram showing the container shown in FIG. 27.
Figure 29:
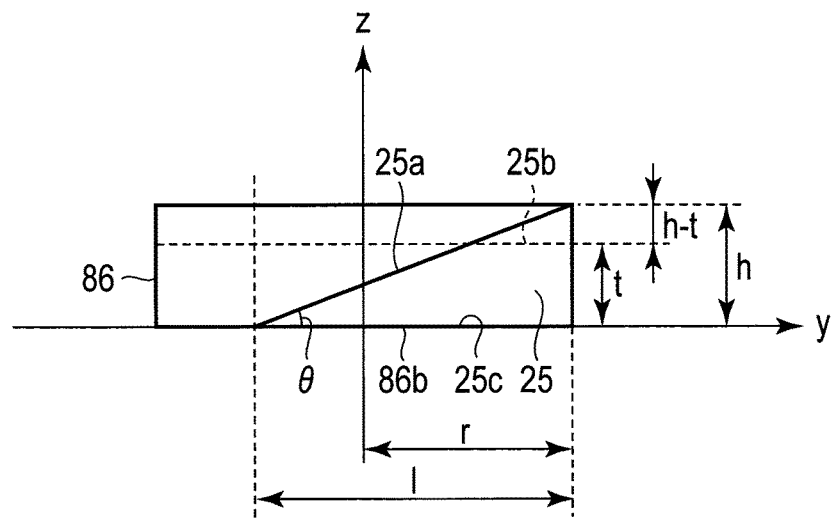
FIG. 29 is a schematic diagram showing a cross section of the container shown in FIG. 27 taken along arrows y and z.
Figure 30:
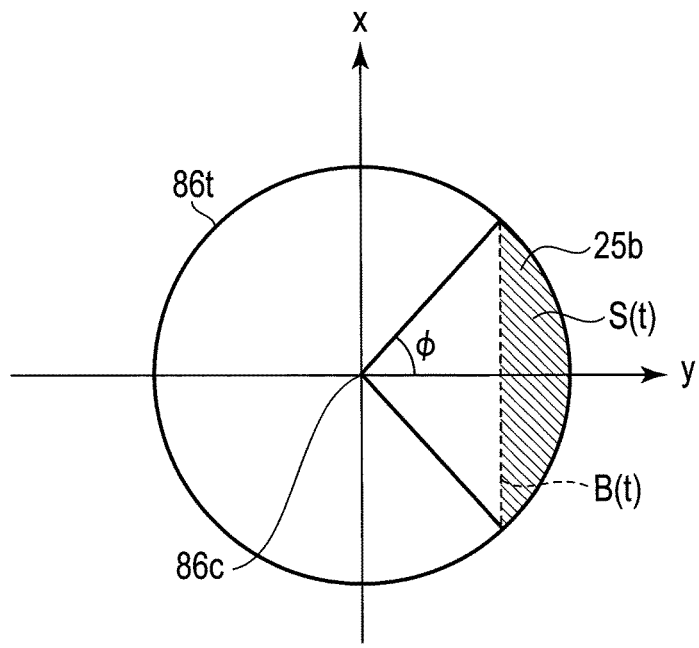
FIG. 30 is a schematic diagram showing a cross section of bottom portion of the container when it is cut in height t.

First, FIGS. 28 to 30 are used to calculate the volume V of the solution 25 in the container 86.

FIG. 28 is a perspective diagram showing the container 86 of FIG. 27.

In the figures, the arrows x, y and z show directions normal to each other. The arrow x indicates a direction which passes through the center of the bottom portion 86b of the container 86 and normal to the arrow y along the bottom portion 86b. The figures also show the surface 25a of the solution and a border line BO between the bottom portion 86b and the surface 25a of the solution 25.

FIG. 29 is a schematic diagram showing a cross section of the container 86 of FIG. 27, taken along the arrows y and z.

In these figures, t represents an arbitrary height of the solution 25 having a height h.

FIG. 30 is a schematic diagram showing a cross section of the bottom portion when the container 86 is cut at height t.

The figures illustrate a bottom portion 86t of the container 86 cut at an arbitrary height t, a center 86c of the bottom portion 86t, a bottom portion 25b of the solution 25 cut at the arbitrary height t, and a a border line B(t) between the surface 25a and the bottom portion 25b. An angle $\phi$ is defined as an angle made between the border line Bt and the center 86c of the bottom portion 86t of the solution in the container 86.

An area S(t) of the bottom portion 25b can be obtained by deducting the area of a triangle of angle 2 $\phi$ from a fan-shaped area of angle 2$\phi$ and can be represented by the following formula (4).

$$S(t) = r^2(\phi - \cos\phi \sin\phi) \quad (4)$$

From FIG. 29, it can be expressed as l=r−r cos $\phi$), and therefore the relationship of the following formula (5) can be induced.

$$\frac{h-t}{h} = \frac{r - r\cos\phi}{l} \quad (5)$$

When the formula (5) is arranged, the following formula (6) can be induced.

$$t = h\left\{1 - \frac{r}{l}(1 - \cos\phi)\right\} \quad (6)$$

When both sides of the formula (6) are differentiated with $\phi$, the following formula (7) is obtained.

$$\frac{dt}{d\phi} = -\frac{hr}{l}\sin\phi \quad (7)$$

Here, the value of the arbitrary height t is in a range from 0 to h, and the value of $\phi$ is in a range from the value represented by the following formula (8) to 0.

$$\phi = \cos^{-1}\left(-\frac{l-r}{r}\right) \to 0 \quad (8)$$

The volume of the solution V is obtained by integrating S(t) in a range from height 0 to h. When this is substituted and integrated using $\phi$ in a range from formula (8) to 0, as represented by the following formula (2'), and thus the right side of the formula (2) can be induced.

$$V = \int_0^h S(t)dt \quad (2')$$
$$= -\frac{hr^3}{l}\int_{\cos^{-1}\left(-\frac{l-r}{r}\right)}^0 (\phi - \cos\phi\sin\phi)d\phi$$
$$= r^3 \tan\theta\left(-\frac{\sin^3\alpha}{3} + \sin\alpha - \alpha\cos\alpha\right)$$

Here, α is shown in the formula (3).

For example, in the case where the container is a dish having a diameter of 35 mm (a height of about 10 mm and an inner diameter of about 17.5 mm), a recommended amount of the solution can be set in a range from 1.8 mL to 2.7 mL.

FIG. 31 is a graph showing the relationship between the angle value θ and the volume V of the solution as a result of numerical analysis of the formula (2).

In the figure, a curve 123 represents the relationship between the inclined angle θ and the volume V of the solution.

Here, it was set as: r=17.5 mm and h=10 mm. In the case of a recommended amount of 2.7 mL of the solution, the inclined angle θ at which the solution spills is 25 degrees, and it is found that at least a static friction coefficient of 0.47 or higher is required.

In practice, a meniscus is created by surface tension, but an experiment using the culture fluid was performed and it was confirmed that an equivalent result can be obtained.

Experiment 1: Measurement of static friction coefficient μ of container and maximum inclination angle As the materials for the support member, aluminum treated with white alumite, ABS resin, styrene-based thermosetting elastomer AR741B (a product of Aronkasei Corporation), styrene-based thermosetting elastomer AR791B (a product of Aronkasei Corporation), a silicone rubber (a durometer hardness of A50) were processed into plate boards, respectively.

A polystyrene dish (P35GG-0-14-C, a product of MatTek Co.) having an outer diameter of 35 mm was placed on each of the boards of the respective materials and was subjected to scanning of inclined angle θ, and thus the maximum inclination angle corresponding to the frictional angle θ0 at which the static frictional force p acts, was experimentally obtained for each material. The experiments were conducted twelve times for each material and an average value excluding the maximum and minimum values was obtained for each. The results thus obtained are shown in Table 1 below.

TABLE 1

| Container | Material | Static frictional coefficient μ | Maximum inclined angle θ [deg] |
|---|---|---|---|
| 35 mm-polystyrene dish | Aluminum (treated with white alumite) | 0.37 | 20.0 |
| 35 mm-polystyrene dish | ABS | 0.40 | 21.8 |
| 35 mm-polystyrene dish | TPE elastomer (741B) | »1 | >45 |

TABLE 1-continued

| Container | Material | Static frictional coefficient μ | Maximum inclined angle θ [deg] |
|---|---|---|---|
| 35 mm-polystyrene dish | TPE elastomer (791B) | 0.55 | 28.6 |
| 35 mm-polystyrene dish | Silicone rubber (Shore A50°) | »1 | >45 |

As shown in Table 1, in the cases of the aluminum board treated with alumite and ABS, generally used in the material for the housing, the static friction coefficient was lower than a required value of 0.47. On the other hand, in the cases of thermoplastic elastomers AR-741B and AR-791B, and a rubber material such as silicone rubber of a durometer hardness of A50, for example, the static friction coefficient was 0.47 or higher. Therefore, when one of these materials is used for the support member, a region where the container does not easily slip can be provided in the placement portion. In particular, AR-741B and the silicone rubber had a static friction coefficient far greater than 1, and the inclination angles thereof were greater than 45°. Therefore, it is considered that the effect of making the container less slidable against the placement portion is higher when these materials are employed.

Herein, the material of the support member was changed, but the static friction coefficient μ depends on each of the material of the support member and the material of the container.

Note that the thermoplastic elastomers and the silicone rubbers are only examples, and the materials with which the container is less slidable are, for example, polyolefin, polyamide, urethane and the like.

(Monitoring Device with Housing Containing Different Materials)

FIG. 32 is a perspective diagram showing the twelfth modified example of the monitoring device according to the first embodiment.

FIG. 33 is a perspective diagram of that shown in FIG. 32 as viewed from a different angle.

Figure 34:
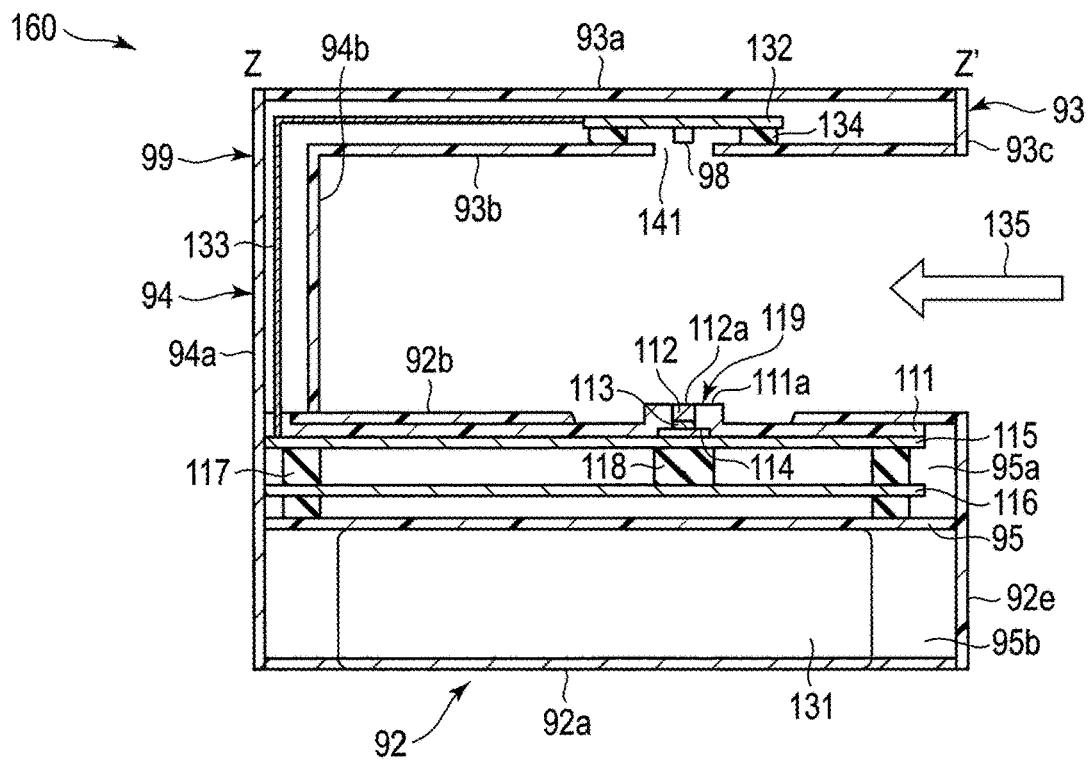
FIG. 34 is a cross section taken along line Z-Z'.

FIG. 34 is a cross section of FIG. 32 taken along line Z-Z'.

When unloading an isothermally adjusted container from the incubator and loading it in the monitoring device, a difference in temperature can be created between inside and outside the container by the heat generated from the electronic circuit parts and the like including the semiconductor optical sensor, which may result in dew condensation on a part of the container. Therefore, there can be a demand of such a monitoring device that can inhibit dew condensation in the container.

As shown, the monitoring device 160 comprises a housing 99. The housing 99 includes a housing body 92 in which a detector provided with a placement portion 111a to place a container containing microbodies thereon, a ceiling portion 93 disposed to oppose the housing body 92 and accommodating a light source 98 for irradiating light onto the microbodies, and a joint portion 94 which connects the ceiling portion 93 and the housing body 92 to each other. The joint portion 94 accommodates wires 133 which electrically connect the light source 98 and a detector 119 to each other.

The housing body 92 is divided into upper and lower chambers of two by a partition plate 95, and the upper chamber 95a accommodates the detector 119, and the lower chamber 95b accommodates a cell battery box 131 electrically connected to the detector 119. The detector 119 includes a second circuit board 114 provided on one main surface of the first circuit board 115, a semiconductor optical sensor 113 provided on the second circuit board 114, a fiber optic plate 112 provided on the semiconductor optical sensor 113 through a pixel array (not shown), and a support member 111 which supports the fiber optic plate 112 and the semiconductor optical sensor 113. The placement portion 111a on which a container can be placed is a part of the support member 111 and is provided around an incident surface 112a of the fiber optic plate 112. On the other main surface of the first circuit board 115, a third circuit board 116 is provided via a spacer 117, on which parts 73 electrically connected to the semiconductor optical sensor 113 by a connector 118, that is, for example, a wireless module, MCU, a memory, and the like are mounted.

The ceiling portion 93 accommodates a ceiling board 132 connected to the wires 133, on which a light source 98 such as an LED is provided. Of the members of the ceiling portion 93, a lower member 93b of the ceiling board 132 comprises an opening 141 for light irradiated from the light source 98 to transmit. The ceiling board 132 is supported by a spacer 134 on the member 93b.

For the housing 99, for example, a board-shaped member can be used. A rectangular member 92a is used for the bottom portion of the housing body 92, and a rectangular member 92b comprising the opening 141 in a section corresponding to at least the placement portion 111a is used in a position opposing the member 92a. Further, for a side surface, which is a front surface as viewed from an arrow 135, a member 92e is used, and a square-U-shaped member 92c is used for the left side surface, and a member 92d having a shape of a line symmetrical with the member 92c is provided in the right side surface. Further, a member 93c is used for a top plate of the ceiling portion 93, and a member 93a is used for a front surface. Between the member 93b of the ceiling portion 93 and the member 92b of the housing body 92, a member 94b of the joining portion 94 is provided. Further, on a back side thereof, the housing body 92 and the member 94a of the joining portion 94 are provided.

In the monitoring device 160, a metal, for example, aluminum can be used as the material of the member 94a and the member 92a, and as the material of the other members, a resin, for example, ABS resin can be used. With this structure, heat generated in the wireless module, MCU, memory and the like implemented on the third substrate 116 in the housing body 92 is released, and thus the temperature difference between inside and outside the container is reduced and the dew condensation in the container can be suppressed.

Note that, in FIG. 34, a metallic material is used as the member 94a and the member 92a, and a resin material is used as the other members, but the embodiment is not limited to this. For example, a first material of a low thermal conductivity, for example resin may be used as a material of the rectangular member 92b which comprising an opening in a section corresponding to at least the placement portion 111a of the members constituting the housing 99, and a second material having a thermal conductivity higher than the thermal conductivity of the first material may be used for at least one of the members other than the member 92b, for example a metal can be used as the second material.

Examples of the first material are resin materials of, for example, ABS, acryl, MC nylon, epoxy, fluorine, PEEK, rubber and the like. Examples of the second material are metallic materials of, for example, aluminum, stainless steel, iron, copper and the like.

(Monitoring Device in which Circuit Board is Provided on the Ceiling Portion)

Figure 35:
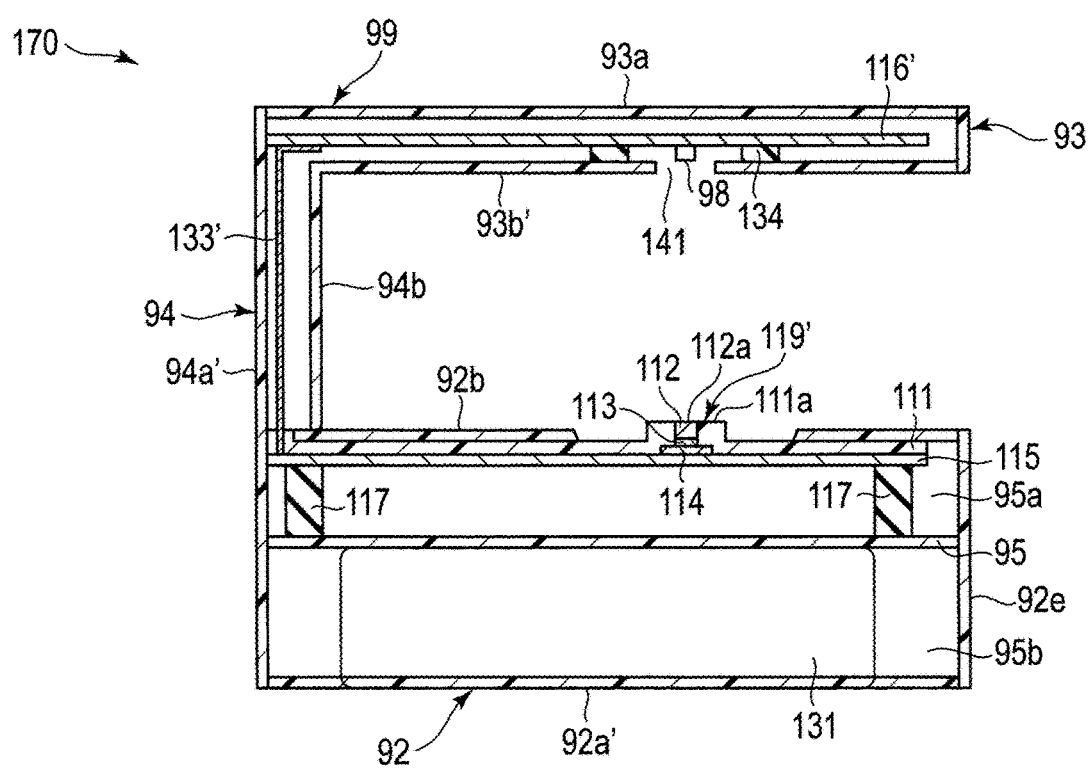
FIG. 35 is a perspective diagram showing the thirteenth modified example of the monitoring device of the first embodiment.

FIG. 35 is a diagram showing the thirteenth modified example of the monitoring device according to the first embodiment.

As shown, a monitoring device 170 comprises a housing 99', and the housing 99' includes a housing body 92' which accommodates a detector provided with a placement portion 111a on which a container containing microbodies is placed, a ceiling portion 93' disposed to oppose the housing body 92' and accommodating a light source 98 which irradiates light onto microbodies, and a joining portion 94 which connects the ceiling portion 93' and the housing body 92' to each other.

The housing body 92' is divided into upper and lower chambers of two by a partition plate 95, and the upper chamber 95a accommodates the detector 119, and the lower chamber 95b accommodates a cell battery box 131 electrically connected to the detector 119. The detector 119 includes a second circuit board 114 provided on one main surface of the first circuit board 115, a semiconductor optical sensor 113 provided on the second circuit board 114, a fiber optic plate 112 provided on the semiconductor optical sensor 113 through a pixel array (not shown), and a support member 111 which supports the fiber optic plate 112 and the semiconductor optical sensor 113. On the other main surface of the first circuit board 115, the partition plate 95 is provided via a spacer 117.

The ceiling portion 93' accommodates a ceiling board 116' connected to the semiconductor optical sensor 113, on which a light source 98 such as LED. On the ceiling board 116', a wireless module, MCU, a memory, and the like are mounted.

As described above, in the monitoring device 160 shown in FIG. 34, the third circuit board on which the parts such as a wireless module, MCU, memory and the like are mounted, is provided in the housing body 92 comprising the placement portion 111a for the container. On the other hand, the monitoring device 170 shown in FIG. 35, these parts are not provided in housing body 92', but provided on the ceiling board 116' accommodated in the ceiling portion 93'. With this structure, the container is spaced away from the parts such as the wireless module, MCU, memory and the like, and therefore the temperature difference between inside and outside the container, which may be caused by heat generation from the parts, can be suppressed, thus making it possible to inhibit dew condensation in the container.

Note that the joining portion 94' accommodates wires 133' which electrically connects the ceiling board 116' on which the light source 98, wireless module, MCU, memory and the like are mounted, to the detector 119.

As the material of the member 92a' and the member 94a', a resin, for example, ABS resin can be applied.

(Another Modification of the Monitoring Device)

In the monitoring device according to the first embodiment described above, cells as microbodies are contained in a container so as to be observed. But in place of accommodating cells in the container 6, for example, a light-transmissive seal or the like is directly applied on the skin and then detached therefrom, to extract horny cells, which may be directly placed on the fiber optic plates 5. In this case, the cells are brought into contact with the fiber optic plates 5, so as to be observed without being through the bottom portion of the container, which may have a certain thickness, and therefore even clearer images can be obtained.

(Monitoring System)

FIG. 20 is a block diagram showing a monitoring system according to the second embodiment.

A monitoring system 120 according to the second embodiment is a system for observing microbodies using the monitoring device according to the first embodiment. As shown, the system comprises light sources 41, detectors 42 which detect scattering light obtained from the light source 41 as light is irradiated onto samples to obtain image data, a communication unit which communicates with a server side and transmits the image data obtained from the detectors to a server 44, and a controller 46 which controls the light sources 41, the detectors 42 and the communication unit 43, which are provided on a node side, and further the server 44 on a server side, which accumulates and analyzes the image. When the microbodies are cells, which are susceptible by heat which may be generated, the light sources 41 and the detectors 42 are placed in a cell culture environment within the structure on the node side, but the controller 46 and the communication unit 43 are placed outside the cell culture environment.

As the light sources 41 and the detectors 42, the light source and the detector employed in the monitoring device of the first embodiment can be used. The detectors 42 each can comprise, for example, as shown in FIG. 1, a semiconductor optical sensor 3, a pixel array 2 provided on the semiconductor optical sensor 3, and fiber optic plates 5 provided on the semiconductor optical sensor 3 via the pixel array 2. The fiber optic plates 5 receives, of the light irradiated on the microbodies, light entering at an angle in a range of ±60 degrees with respect to the fiber axis of the fiber optic plates, to transfer to the semiconductor optical sensor 3 so as to form the images.

With the monitoring system 120, when the user requests image data from a terminal 45 such as a smart phone or a tablet, the server 44 transmits a trigger signal to the communication unit 43. The communication unit 43 gives the trigger signal to acquire image data, to the controller 46. Here, the controller 46 is set in an image acquisition mode, in which the light source 41 is controlled to be turned on to irradiate light onto microbodies as the samples, and the detector 42 detects the obtained scattering light and acquires the image data. The image data thus acquired is sent to the controller 46, so as to be transmitted to the communication unit 43 as the image data for communication. The communication unit 43 sends the image data to the server 44, and the image data, its analytical data and the like can be accumulated in the server 44. Thus, in reply to requests from the terminal 45, the server 44 can acquire and transmit image data.

Moreover, when the monitoring system 120 is set in advance by using the automatic reception function of the terminal, to receive image data by a certain period of time, image data can be periodically acquired.

Furthermore, it can set up by using the automatic reception function of the terminal such as to notify an alert when an abnormality is detected in analytical data by e-mail or screen display.

Examples of the analytical data are quantitative values of the degree of cell growth from the number of cells or the occupation area ratio, quantitative values of the degree of cell activity from fluorescent data, and quantitative values of the pH concentration of culture fluid from the color of an indicator (such as Phenol Red) in the culture fluid.

(Monitoring System which Carry Out Management and Analysis of Data of Microscope, Cell Counter and Monitoring Device)

For operators performing cell culturing, it is important to manage dispersion of cells in terms of success in research and the quality of products. However, the cells are sensitive to not only the dispersion caused by an intracellular cause but also to the environmental factor and work procedural factor. Under these circumstances, the operators are required to carefully manage the culturing conditions and confirm using microscopes frequently.

It is important to record and store data associated with the cultures. Here, it is difficult to take notes of a wide variety of items in an experiment notebook by handwriting, and therefore it has become a common procedure to take record of only minimum items considered to be necessary at that time (for example, cell type, generation, time and date, and the like).

Here, the data on the shape of cells monitored a microscope and the data such as the number of cells, the life and death ratio and the like, measured with a cell counter are examples of the information which may not be kept as records because it is troublesome and burdensome to associated digital data and the experimental notebook with each other in terms of procedure. However, when some abnormality occurs once, there can rise a situation in which items which have not been recorded need to be objects to be verified.

Further, the handwritten or printed records such as experiment notebooks are poor in searchability, and it is not also easy to compare a plurality of data items.

Under these circumstances, in addition to the monitoring system of FIG. 20, a monitoring system which can manage data obtained by a microscope or cell counter for analysis is obtained.

FIG. 36 is a diagram showing a structure of another example of the monitoring system according to the second embodiment.

Figure 37:
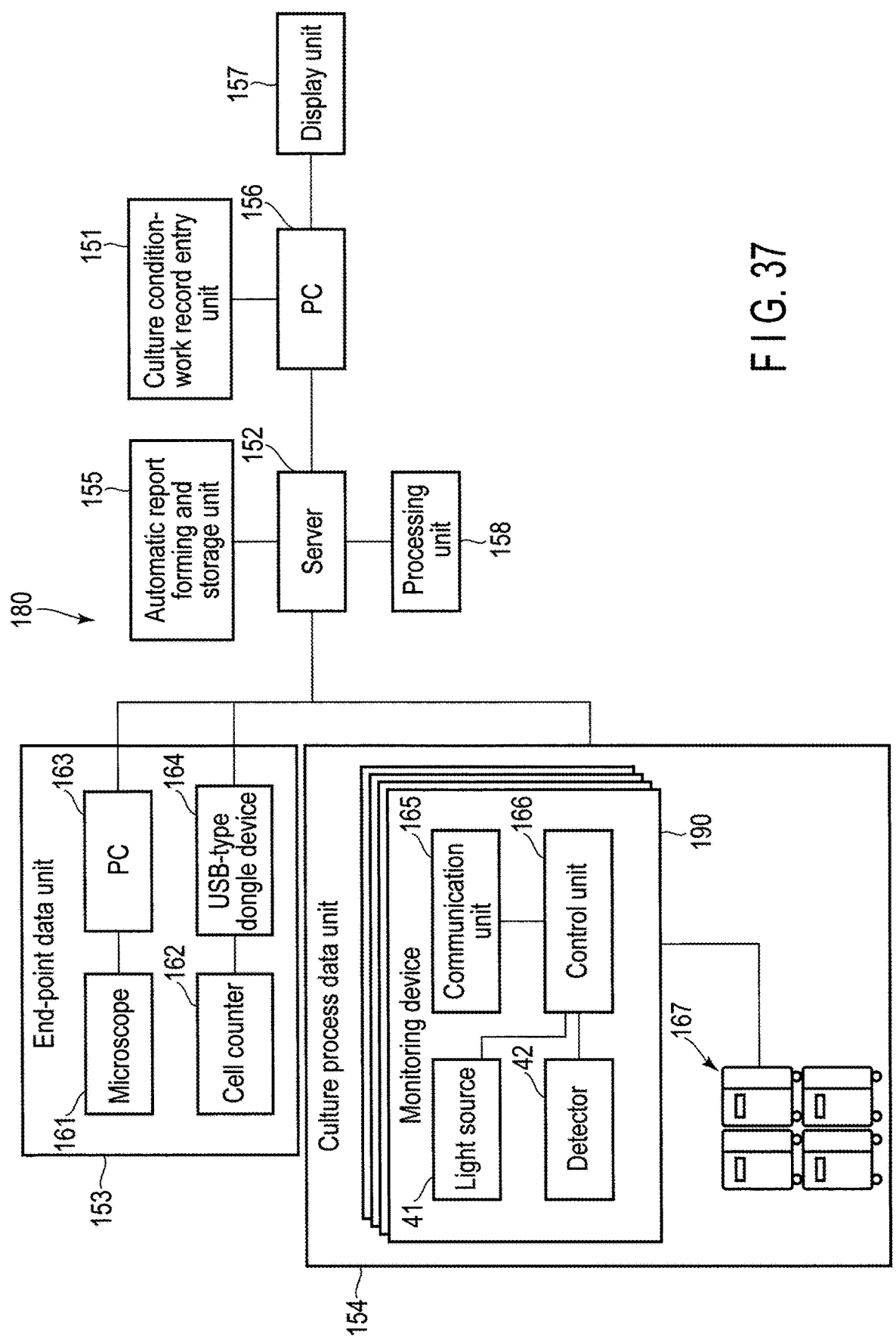
FIG. 37 is a block diagram showing the monitoring system shown in FIG. 36.

FIG. 37 is a block diagram showing the monitoring system of FIG. 36.

As shown in FIGS. 36 and 37, a monitoring system 180 is a system which manages and analyzes the measurement data of, for example, a culture cell microscope, cell counter and monitoring device, and includes a culture condition-work record entry unit 151 configured to enter culture conditions such as a cell type, culture fluid, dish and the like and its work record, an end-point data unit 153 to observe the shape, number, life and death ratio and the like of culture cells at a predetermined time, a culture process data unit 154 to monitor real-time abnormality, time for doubling, adhesion time and the like while culturing cells under predetermined culture conditions, and an automatic report forming and storage unit 155 to automatically form and store reports on management of cell lots used, comparison with culture results of the past and visualization of progress and the like.

For the culture condition-work record entry unit 151, for example, a terminal such as a personal computer (PC) or a tablet can be used, and here, a terminal of PC 156 is used here. The PC 156 comprises a display 157 and it can be connected to, through a server 152, the end point data unit 153, the culture process data unit 154, a processing unit 158 to acquire and analyze measurement data obtained in the end point data unit 153 and the culture process data unit 154, and the automatic report forming and storage unit 155.

Examples of the information to be entered by the operator from the entry unit 151 are the cell type, generation (passage number), type of culture container used, coating applied on the culture container, cell culture fluid, serum added to cell culture fluid, dates and times when culture is started and finished and the like. Further, a function that can select a culture condition employed in the past as a template is provided, and thus operations of the entry can be omitted. The PC 156 is used to handle input data and send them to the server 152.

The end point data unit 153 includes a microscope 161, a PC 163 connected to the microscope 161 and communicable with the server 152, a cell counter 162 and a dongle device 164 connected to the server 152 and communicable with the cell counter 162.

The data on the results of culture obtained in the end point data unit 153 includes image data of the cells photographed with the microscope 161 and measurement data such as cell concentration, the number of cells, the life and death ratio and the like measured with the cell counter 162.

In many cases, a general cell counter is equipped with a function of data output to a USB memory. Here, an exclusive USB type dongle device is connected to the cell counter 162, and the data acquired from the cell counter 162 can be collected in the server 152. The USB-type dongle device can be defined as a device equipped with a USB memory function, a wireless communication function and a transmission/reception script execution function. For example, using a USB type dongle device, writing of data from the cell counter is detected and the data can be can be automatically uploaded to the server 152.

When using a microscope connected to a terminal such as a PC or the like, equipped with a camera, the data acquired with the microscopy, stored in a storage holder of the PC can be collected in the on-line server 152. When using a microscope connected to a terminal such as a PC or the like, which is equipped with a camera but not connected to a network, the USB type dongle device is used to collect the acquired data in the server 152.

When using a microscope not equipped with a camera, a digital camera is attached thereto with an attachment (commercially available) for attaching a digital camera to an ocular lens, and with a memory card with a function to connect to a network, that is, for example, Flash Air (registered trademark), and the acquired data can be collected in the server 152.

The culture process data unit 154 includes a light source 41, a detector 42 which detects scattered light obtained, for example, by irradiating light onto a sample from the light source 41 to obtain image data, a communication unit 43 which communicates with the server 152 and sends image data obtained from the detector 42 to the server 152, and a control unit 46 which controls the light source 41, the detector 42 and the communication unit 43. As the light source 41 and the detector 42, the light source and the detector used for the monitoring device of the first embodiment can be used as in the monitoring system shown in FIG. 20. The detector 42 may comprise a semiconductor optical sensor 3, a pixel array 2 provided on the semiconductor optical sensor 3, and an image transfer element 5, for example, a fiber optic plate, provided on the semiconductor optical sensor 3 via the pixel array 2 as shown in FIG. 1.

In the culture process data unit 154, the real-time cell image data acquired by the detector 42 of the monitoring device 190 can be obtained. By analyzing the sequential image data with the processing unit 58, the data which represent the state of the cells such as the doubling time, adhesion time, movement and the life and death of the cells, estimated from the movement can be acquired. The acquired data can be collected in the server 152 from the processing unit 158. The culture process data unit 154 can be connect to a $CO_2$ incubator 167 via a network, and the data on the $CO_2$ concentration, $O_2$ concentration, temperature and humidity are acquired from the $CO_2$ incubator 167, and then can be automatically uploaded by the communication unit 165 to the server 152.

The real-time cell image data and the data of the $CO_2$ concentration, $O_2$ concentration, temperature and humidity in the $CO_2$ incubator 167 can be uploaded by the communication unit 165 to the server 152.

Further, with the server 152, an alert can be made in real time based on the acquired data on the state of cells. Examples of the items for the alert are that the number of cells or confluency has reached a threshold, that the doubling time exceeds or is less than a threshold and that the adhesion time exceeds or is less than a threshold. With the server 152, it can be set using an auto-receipt function of the PC 156 to notify an alert by reception of an mail or image display on a display 157 or the like, when an item to be alerted is detected.

Automatic formation of reports and reporting in the accumulation unit 155 are carried out on-line in the server 152.

FIG. 38 shows the first example of the report image.

The data on the reported culture results can be acquired from the server 152. As shown, for example, a first column 181 of a report image 171 can indicate the operator and culture conditions of a cell culture test ID: A. Here, for example, cell type: HeLa, generation number: 3, culture container: 10 cm dish, coating: collagen, cell culture liquid: DMEM, serum: bovine serum, culture start time and date: 2020 Jan. 3 9:00 and culture end time and date: 2020 Jan. 6 9:00.

Under the first column 181, a second column 182, a third column 183 and a fourth column 184 each can indicate end point data and culture process data and the like, associated with the data registration day and time.

Here, for example, the second column 182 indicates the results of measurement of the cell counter on the first day, that is, cell concentration: $2\times10^6$ cells/mL, life and death rate: 80%, measurement time: 2020 Jan. 3 8:30. Further, the third column 183 indicates the microscopic image data and capture time on the second day. Moreover, the fourth column 184 indicates the microscopic image data and capture time on the fourth day and the results of measurement by the cell counter, that is, cell concentration: $2\times10^6$ cells/mL, life and death rate: 80%, measurement time: 2020 Jan. 6 9:30.

Furthermore, the operator can add comments in blanks 191, 192 and 193 provided for the respective columns. For example, here, the blank 191 notes that dissemination was carried out after 10-fold dilution.

FIG. 39 shows the second example of the report image.

As shown, next to the first column 181, second column 182, third column 183 and fourth column 184, a fifth column 281, a sixth column 282, a seventh column 283 and an eighth column 284 are provided, respectively, and for a cell culture test ID: B to be compared with the culture test ID: A, the fifth column 281 indicates the culture conditions, and the sixth column 282, the seventh column 283 and the eighth column 284 indicate the end point data, culture process data and the like, associated with the data registration time. Further, comparison results with the data of culture tests of the past and those carried out at the same time can be indicated as well.

For example, the fifth column 281 indicates the culture conditions, that is, cell type: HeLa, generation: 5, culture container: 10 cm dish, coating: collagen, cell culture liquid: DMEM, serum: bovine serum, culture start date and time: 2020 Jan. 9 9:00, and culture end date and time: 2020 Jan. 12 9:00.

Further, the sixth column 282 indicates the results of measurement by the cell counter on the first day, that is, cell concentration: $2\times10^6$ cells/mL, life and death ratio: 80%, and measurement time: 2020 Jan. 9 8:30. The seventh column 283 indicates the microscopic image data and capture time on the second day. Further, the eighth column 284 indicates the microscopic image data and capture time and the results of measurement by the cell counter on the fourth day, that is, cell concentration: $2\times10^6$ cells/mL, life and death rate: 60% and the measurement time: 2020 Jan. 12 9:30.

Further, the operator can add comments to the blanks 194, 195 and 196 provided for the respective columns. For example, here, the blank 194 notes that dissemination was carried out after 10-fold dilution.

Figure 40:
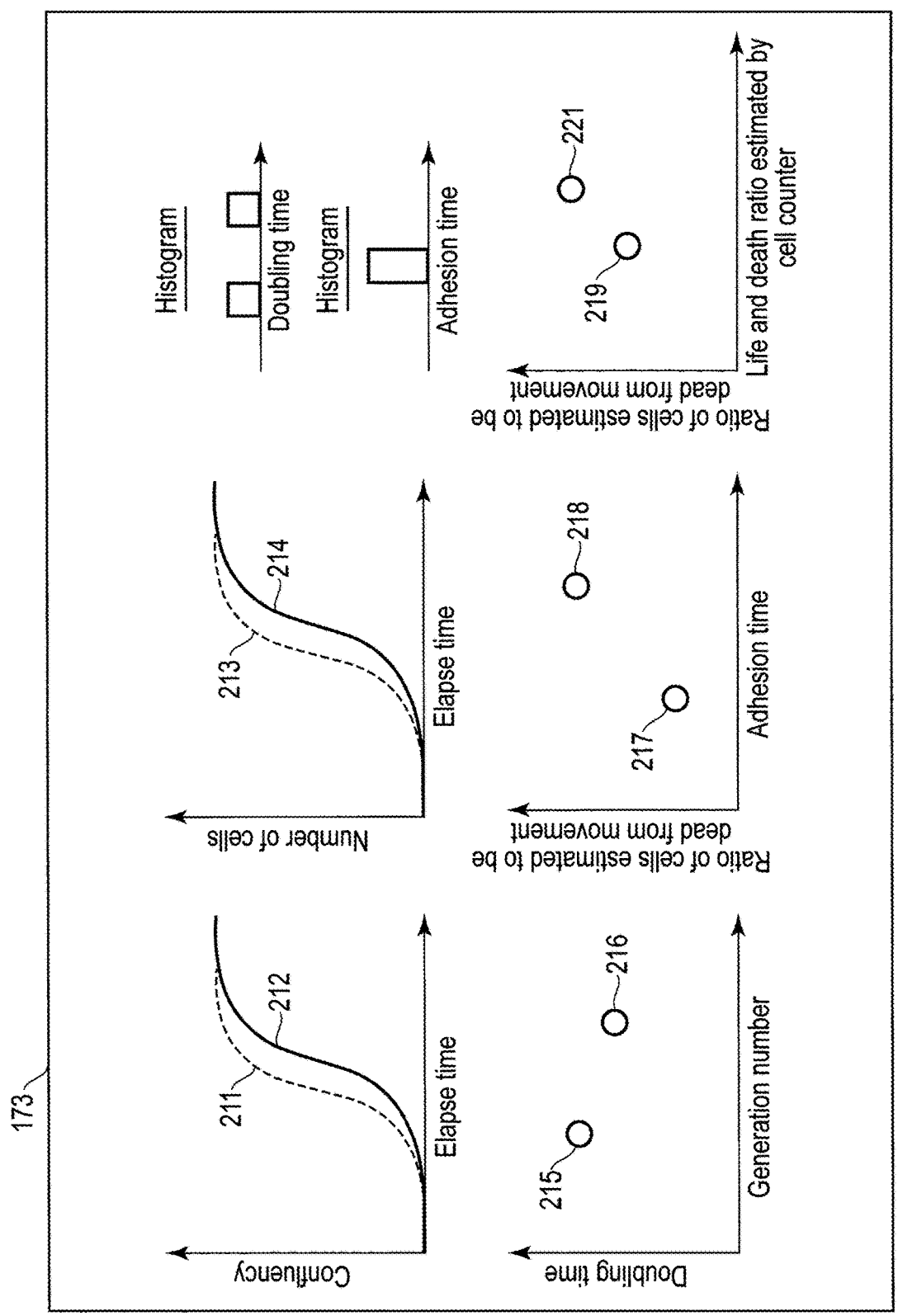
FIG. 40 is a diagram showing the third example of the report image.

FIG. 40 shows the third example of the report image.

As to the culture test ID: A and culture test ID: B shown in FIG. 39, the comparison results on the report image 173 can be presented by way of sequential progression, histograms for separate items, correlation diagrams each between two items or more, and the like.

As shown, in terms of the sequential progression, for example, a graph representing the relationship between elapsed time and confluency and a graph representing the relationship between elapsed time and number of cells for culture test ID: A and culture test ID: B may be used. Further, in terms of the histograms for separated items, a histogram of the doubling time and a histogram of the adhesion time. Furthermore, in terms of the correlation diagrams each between two items or more, a correlation diagram between generation number and doubling time, a correlation diagram between adhesion time and the ratio of cells estimated to be dead from the movement, and a correlation diagram between the life and death ratio estimated by the cell counter and the ratio of cells estimated to be dead from the movement can be provided.

In the figures, numerals 211, 213, 215, 217 and 219 indicate the results of the culture test ID: A, and numerals 212, 214, 216, 218 and 221 indicate the results of the culture test ID: A.

Moreover, there may be a function in which a supervisor can approve the contents of a report.

Furthermore, there may be a function to share the report with a third party such as a co-researcher as a link.

By acquiring the culture process data in addition to the end point data, the results of culture of cells can be compared quantitatively with each other over a variety of items. Furthermore, by comparing a large number of results of the culturing tests, items of high correlation between items or indexes obtained by analyzing the items can be clarified. For example, based on the life and death ratio measured by the cell counter, the algorithm for estimating the life and death of cells can be improved in the analysis of the sequential images of the culture process data.

As described above, with use of the monitoring system 180, the culture conditions and work records can be recorded online, and the end point data and culture process data are collected online, to report the result. In this manner, in the culture of cells, the dispersion of cells due to endogenous factor of the cells, the environmental factor, the dispersion of cells due to the operator's technical factor can be managed, and thus the culture conditions can be well adjusted, making it possible to improve the quality of the product.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A monitoring device comprising:
a plurality of detectors which observe two or more independent areas of a light-transmissive base material including a plurality of the independent areas on each of which a microbody is placed,
wherein each of the detectors includes an image transfer element including an incident surface which allows light to enter from the light-transmissive base material and an emission surface which emits the light entering from the incident surface and transferring two-dimensional image data of the microbody, and a semiconductor optical sensor which receives light from the emission surface.

2. The device of claim 1, wherein
each of the detectors further includes a support member which supports the image transfer element and the semiconductor optical sensor,
the support member comprises a placement portion on which the base material is to be placed, and
the placement portion includes an end portion flush with the incident surface.

3. The device of claim 2, wherein
the placement portion comprises a first projecting portion including a first end portion surrounding the incident surface of the image transfer element, at least a part of which is flush with the incident surface, and a second projecting portion including a second end portion spaced apart from the first projecting portion, at least a part of which is flush with the incident surface.

4. The device of claim 3, wherein
the placement portion further comprises a third projecting portion including a third end portion, at least a part of which is flush with the incident surface,
the second end portion and the third end portion are each formed into a semi-circular ring shape, and
the second projecting portion and the third projecting portion are disposed to surround the first projecting portion with an interval therebetween.

5. The device of claim 2, wherein
the base material is a bottom portion of a container, and the microbody and a solution are contained in the container, and
the placement portion includes a region where a static friction coefficient μ between the end portion of the placement portion and the bottom portion of the container containing the solution when the container is inclined at an friction angle θ at which the container starts to slide, satisfies a relationship represented by a following formula (1):

$$\mu = \tan \theta 0 \quad (1).$$

6. The device of claim 1, further comprising:
a parallel light source provided on the base material; and
an optical filter provided between the image transfer element and the semiconductor optical sensor and shielding light of a predetermined wavelength.

7. The device of claim 1, further comprising:
a substrate on which the detectors are provided,
wherein
the base material is a container which contains a solution containing the microbody, and
the device further comprises a light source provided on the substrate so as to irradiate light to be reflected by a surface of the solution, onto the microbody.

8. The device of claim 7, further comprising a reflector which reflects the light, above the container.

9. The device of claim 1, further comprising a housing accommodating the detectors,
wherein
the housing comprises a first region surrounding the incident surface, on which the base material can be placed, and a second region which is a region other than the first region,
at lease a part of the second region is formed from a second material different from a first material of the first region, and the second material has a thermal conductivity higher than a thermal conductivity of the first material.

10. The device of claim 1, further comprising a housing accommodating the detectors,
wherein
the housing comprises:
a housing body accommodating the image transfer element and the semiconductor optical sensor, on which the base material on which the microbody is placeable, can be placed, and
a ceiling portion disposed to oppose the housing body and accommodating a light source which can irradiate light onto the microbody and a circuit board on which parts electrically connected to the semiconductor optical sensor are mounted.

11. The device of claim 1, further comprising a substrate configured to be provided the detectors, and two or more stages of combinations of the substrate, the detectors provided on the substrate, and the base material provided on the detectors, are stacked one on another.

12. The device of claim 11, further comprising a light source provided on a surface opposite to a surface on which the detectors are provided, of each of the substrates of a second stage or higher, to oppose base material of one stage lower.

13. The device of claim 1, wherein
the detectors further include support members each supports the image transfer element and the semiconductor optical sensor, and the support member comprises a placement portion on which the base material is placed, the placement portion includes an end portion flush with the incident surface, and the incident surface and an end portion of adjacent ones of the detectors are flush with each other.

14. The device of claim 1, further comprising a horizontal drive mechanism which supports at least the semiconductor optical sensor to be horizontally movable.

15. The device of claim 1, wherein
the image transfer element is a fiber optic plate, an SELFOC lens or an SELFOC lens array.

16. The device of claim 15, wherein
the image transfer element is a fiber optic plate, and the fiber optic plate receives light of light irradiated on the microbody, light entering the fiber optic plate at an angle in a range of ±60 degrees with respect to a fiber axis thereof, and transmit the light to the semiconductor optical sensor.

17. The device of claim 15, wherein
the image transfer element is a fiber optic plate, which further includes
a first light source irradiating light onto the microbody at a first angle with respect to a fiber axis of the fiber optic plate, and
a second light source irradiating light onto the microbody at a second angle different from the first angle, to the fiber axis of the fiber optic plate, provided on the base material.

18. A monitoring system comprising:
a monitoring device comprising a plurality of detectors which observe two or more independent areas of a light-transmissive base material including a plurality of the independent areas on each of which a microbody is placed,
wherein each of the detectors includes an image transfer element comprising an incident surface which can receive light from the light-transmissive base material and an emission surface which emits light incident on the incident surface, which transfers two-dimensional image data of the microbody to a semiconductor optical sensor, and the semiconductor optical sensor which receives light from the emission surface; and
a controller configured to send image data obtained from the detector unit detectors of the monitoring device a to control a server which stores and analyzes image data from the controller.

19. The system of claim 18, further comprising a culture process data device comprising the monitoring device, the controller, and a server storing data from the controller, the system further comprising:
an end point data device including a microscope and a cell counter;
a processor configured to analyze data obtained by the culture process data device and the end point data device;
an automatic report forming device which automatically forms reports based on the data obtained by the culture process data device, the end point data device and the processor; and
a storage connected to the automatic report forming device.

20. The system of claim 19, wherein
the end point data device further comprises a USB-type dongle device connected to the cell counter and comprising a USB memory function, a wireless communication function and a transmission/reception script execution function.

21. The system of claim 18, wherein
each of the detectors further includes a support member which supports the image transfer element and the semiconductor optical sensor,
the support member comprises a placement portion on which the base material is to be placed, and
the placement portion includes an end portion flush with the incident surface.

22. The system of claim 21, wherein
the placement portion comprises a first projecting portion including a first end portion surrounding the incident surface of the image transfer element, at least a part of which is flush with the incident surface, and a second projecting portion including a second end portion spaced apart from the first projecting portion, at least a part of which is flush with the incident surface.

23. The system of claim 22, wherein
the placement portion further comprises a third projecting portion including a third end portion, at least a part of which is flush with the incident surface,
the second end portion and the third end portion are each formed into a semi-circular ring shape, and
the second projecting portion and the third projecting portion are disposed to surround the first projecting portion with an interval therebetween.

24. The system of claim 21, wherein
the base material is a bottom portion of a container, and the microbody and a solution are contained in the container, and
the placement portion includes a region where a static friction coefficient $\mu$ between the end portion of the placement portion and the bottom portion of the container containing the solution when the container is inclined at an friction angle $\theta$ at which the container starts to slide, satisfies a relationship represented by a following formula (1):

$$\mu = \tan\theta 0 \tag{1}$$

25. The system of claim 21, wherein
the detectors each further comprise a support member which supports the respective image transfer element and the respective semiconductor optical sensor,
each of the support members comprises a placement portion on which the base material is to be placed,
the placement portion includes an end portion flush with the incident surface, and
the incident surface and end portion of each adjacent pair of detectors are flush with each other.

26. The system of claim 18, further comprising:
a parallel light source provided on the base material; and
an optical filter provided between the image transfer element and the semiconductor optical sensor and shielding light of a predetermined wavelength.

27. The system of claim 18, further comprising:
a substrate on which the detectors are provided,
wherein
the base material is a container which contains a solution containing the microbody, and
the system further comprises a light source provided on the substrate so as to irradiate light to be reflected by a surface of the solution, onto the microbody.

28. The system of claim 27, further comprising a reflector which reflects the light, above the container.

29. The system of claim 18, further comprising a housing accommodating the detectors,
wherein
the housing comprises a first region surrounding the incident surface, on which the base material can be placed, and a second region which is a region other than the first region,
at lease a part of the second region is formed from a second material different from a first material of the first region, and the second material has a thermal conductivity higher than a thermal conductivity of the first material.

30. The system of claim 18, further comprising a housing accommodating the detectors,
wherein
the housing comprises:
a housing body accommodating the image transfer element and the semiconductor optical sensor, on which the base material on which the microbody is placeable, can be placed, and
a ceiling portion disposed to oppose the housing body and accommodating a light source which can irradiate light onto the microbody and a circuit board on which parts electrically connected to the semiconductor optical sensor are mounted.

31. The system of claim 18, further comprising a substrate on which the detectors are disposed, and two or more stages of combinations of the substrate, the detectors provided on the substrate, and the base material provided on the detectors, are stacked one on another.

32. The system of claim 18, further comprising a light source provided on a surface opposite to a surface on which the detectors are provided, of each of substrates of a second stage or higher, to oppose base material of one stage lower.

33. The system of claim 18, further comprising:
a horizontal drive mechanism which supports at least the semiconductor optical sensor so as to be horizontally movable.

34. The system of claim 18, wherein
the image transfer element is a fiber optic plate, an SELFOC lens or an SELFOC lens array.

35. The system of claim 34, wherein
the image transfer element is a fiber optic plate, and the fiber optic plate receives light of light irradiated on the microbody, made incident on at an angle in a range of ±60 degrees to a fiber axis of the fiber optic plate to transmit to the semiconductor optical sensor.

36. The system of claim 34, wherein
the image transfer element is a fiber optic plate, which further includes a first light source irradiating light onto the microbody at a first angle with respect to a fiber axis of the fiber optic plate and a second light source irradiating light onto the microbody at a second angle different from the first angle, to the fiber axis of the fiber optic plate, provided on the base material.

* * * * *